(12) United States Patent
O'Neill et al.

(10) Patent No.: US 8,268,100 B2
(45) Date of Patent: *Sep. 18, 2012

(54) LASER-PRODUCED POROUS SURFACE

(75) Inventors: William O'Neill, Liverpool (GB);
Christopher J. Sutcliffe, Liverpool
(GB); Eric Jones, Limerick (IE)

(73) Assignee: Howmedica Osteonics Corp., Mahwah, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 12/843,376

(22) Filed: Jul. 26, 2010

(65) Prior Publication Data

US 2010/0291286 A1    Nov. 18, 2010

Related U.S. Application Data

(63) Continuation of application No. 12/386,679, filed on Apr. 22, 2009, which is a continuation of application No. 10/704,270, filed on Nov. 7, 2003, now Pat. No. 7,537,664.

(60) Provisional application No. 60/424,923, filed on Nov. 8, 2002, provisional application No. 60/425,657, filed on Nov. 12, 2002.

(51) Int. Cl.
*C21D 1/09* (2006.01)
*B22F 1/00* (2006.01)
*B22F 3/11* (2006.01)
*B32B 15/01* (2006.01)

(52) U.S. Cl. ............. 148/525; 148/513; 148/516; 419/2

(58) Field of Classification Search ............... 75/228, 75/245–250, 10.13; 148/512–514, 516, 524, 148/525, 527–536; *B22F 3/11, 3/105*
See application file for complete search history.

(56) References Cited

U.S. PATENT DOCUMENTS 14,403 A    3/1856    Brown et al.
(Continued)

FOREIGN PATENT DOCUMENTS

CA    2295896 A1    7/2000
(Continued)

OTHER PUBLICATIONS

R. Morgan, C.J. Sutcliffe, W. O'Neill, "Experimental investigation of nanosecond pulsed Nd:YAG laser re-melted pre-placed powder beds," Rapid Prototyping Journal, vol. 7, No. 3, 2001, pp. 159-172.*

(Continued)

*Primary Examiner* — Scott Kastler
*Assistant Examiner* — Vanessa Luk
(74) *Attorney, Agent, or Firm* — Lerner, David, Littenberg, Krumholz & Mentlik, LLP

(57) ABSTRACT

A method of fabricating a porous or partially porous three-dimensional metal article for use as a tissue ingrowth surface on a prosthesis. The porous article is formed using direct laser remelting in a cross section of a layer of metallic powder on a build platform without fusing thereto. The power, speed, spot size and beam overlap of the scanning laser is coordinated so that a predetermined porosity of the metallic powder can be achieved. Laser factors also vary depending from the thickness of the powder layer, type of metallic powder and size and size distribution of the powder particles. Successive depositing and remelting of individual layers are repeated until the article is fully formed by a layer-by-layer fashion. In an additional embodiment, a first layer of metallic powder may be deposited on a solid base or core and fused thereto.

15 Claims, 28 Drawing Sheets

U.S. PATENT DOCUMENTS

| | | |
|---|---|---|
| 2,222,687 A | 12/1879 | Fresco |
| 2,373,769 A | 4/1945 | Macy |
| 3,520,099 A | 7/1970 | Mattes |
| 3,556,918 A | 1/1971 | Lemelson |
| 3,605,123 A | 9/1971 | Pratt et al. |
| 3,806,961 A | 4/1974 | Muller |
| 3,816,855 A | 6/1974 | Saleh |
| 3,826,054 A | 7/1974 | Culpepper, Jr. |
| 4,047,349 A | 9/1977 | Aguilar, Jr. |
| 4,085,466 A | 4/1978 | Goodfellow et al. |
| 4,154,040 A | 5/1979 | Pace |
| 4,164,794 A | 8/1979 | Spector et al. |
| 4,202,055 A | 5/1980 | Reiner et al. |
| 4,218,494 A | 8/1980 | Belmondo et al. |
| 4,305,340 A | 12/1981 | Iwaki et al. |
| 4,344,193 A | 8/1982 | Kenny |
| 4,385,404 A | 5/1983 | Sully et al. |
| 4,444,818 A | 4/1984 | Tominaga et al. |
| 4,502,161 A | 3/1985 | Wall |
| 4,513,045 A | 4/1985 | Bondoc et al. |
| 4,543,158 A | 9/1985 | Bondoc et al. |
| 4,636,219 A | 1/1987 | Pratt et al. |
| 4,644,942 A | 2/1987 | Sump |
| 4,673,408 A | 6/1987 | Grobbelaar |
| 4,714,473 A | 12/1987 | Bloebaum |
| 4,714,474 A | 12/1987 | Brooks, Jr. et al. |
| 4,719,908 A | 1/1988 | Averill et al. |
| 4,766,029 A | 8/1988 | Brock et al. |
| 4,863,538 A | 9/1989 | Deckard |
| 4,944,817 A | 7/1990 | Bourell et al. |
| 4,961,154 A | 10/1990 | Pomerantz et al. |
| 4,969,302 A | 11/1990 | Coggan et al. |
| 4,969,907 A | 11/1990 | Koch et al. |
| 4,990,163 A | 2/1991 | Ducheyne et al. |
| 5,004,476 A | 4/1991 | Cook |
| 5,017,753 A | 5/1991 | Deckard |
| 5,024,670 A | 6/1991 | Smith et al. |
| 5,031,120 A | 7/1991 | Pomerantz et al. |
| 5,034,186 A | 7/1991 | Shimamune et al. |
| 5,053,090 A | 10/1991 | Beaman et al. |
| 5,067,964 A | 11/1991 | Richmond et al. |
| 5,076,869 A | 12/1991 | Bourell et al. |
| 5,080,674 A | 1/1992 | Jacobs et al. |
| 5,090,174 A | 2/1992 | Fragale |
| 5,108,432 A | 4/1992 | Gustavson |
| 5,108,441 A | 4/1992 | McDowell |
| 5,147,402 A | 9/1992 | Bohler et al. |
| 5,155,324 A | 10/1992 | Deckard et al. |
| 5,158,574 A | 10/1992 | Stone |
| 5,171,282 A | 12/1992 | Pequignot |
| 5,176,710 A | 1/1993 | Hahn et al. |
| 5,192,328 A | 3/1993 | Winters |
| 5,219,362 A | 6/1993 | Tuke et al. |
| 5,282,861 A | 2/1994 | Kaplan |
| 5,282,870 A | 2/1994 | Moser et al. |
| 5,287,435 A | 2/1994 | Cohen et al. |
| 5,314,478 A | 5/1994 | Oka et al. |
| 5,323,954 A | 6/1994 | Shetty et al. |
| 5,336,518 A | 8/1994 | Narayanan et al. |
| 5,356,433 A | 10/1994 | Rowland et al. |
| 5,358,529 A | 10/1994 | Davidson |
| 5,368,602 A | 11/1994 | de la Torre |
| 5,386,500 A | 1/1995 | Pomerantz et al. |
| 5,398,193 A | 3/1995 | deAngelis |
| 5,425,210 A | 6/1995 | Zafir |
| 5,443,510 A | 8/1995 | Shetty et al. |
| 5,443,518 A | 8/1995 | Insall |
| 5,461,839 A | 10/1995 | Beck |
| 5,486,599 A | 1/1996 | Saunders et al. |
| 5,490,962 A | 2/1996 | Cima et al. |
| 5,496,372 A | 3/1996 | Hamamoto et al. |
| 5,504,300 A | 4/1996 | Devanathan et al. |
| 5,514,183 A | 5/1996 | Epstein et al. |
| 5,526,627 A | 6/1996 | Beck |
| 5,549,700 A | 8/1996 | Graham et al. |
| 5,571,185 A | 11/1996 | Schug |
| 5,571,196 A | 11/1996 | Stein |
| 5,609,646 A | 3/1997 | Field et al. |
| 5,616,294 A | 4/1997 | Deckard |
| 5,624,463 A | 4/1997 | Stone et al. |
| 5,632,745 A | 5/1997 | Schwartz |
| 5,640,667 A | 6/1997 | Freitag et al. |
| 5,648,450 A | 7/1997 | Dickens, Jr. et al. |
| 5,681,354 A | 10/1997 | Eckhoff |
| 5,702,448 A | 12/1997 | Buechel et al. |
| 5,728,162 A | 3/1998 | Eckhoff |
| 5,729,946 A | 3/1998 | Beck |
| 5,735,903 A | 4/1998 | Li et al. |
| 5,749,874 A | 5/1998 | Schwartz |
| 5,769,899 A | 6/1998 | Schwartz et al. |
| 5,773,789 A | 6/1998 | Devanathan et al. |
| 5,776,201 A | 7/1998 | Colleran et al. |
| 5,782,908 A | 7/1998 | Cahalan et al. |
| 5,795,353 A | 8/1998 | Felt |
| 5,824,098 A | 10/1998 | Stein |
| 5,824,102 A | 10/1998 | Buscayret |
| 5,839,247 A | 11/1998 | Beck |
| 5,857,303 A | 1/1999 | Beck et al. |
| 5,866,113 A | 2/1999 | Hendriks et al. |
| 5,879,387 A | 3/1999 | Jones et al. |
| 5,879,398 A | 3/1999 | Swarts et al. |
| 5,928,285 A | 7/1999 | Bigliani et al. |
| 5,973,222 A | 10/1999 | Devanathan et al. |
| 5,987,838 A | 11/1999 | Beck |
| 5,989,472 A | 11/1999 | Ashby et al. |
| 6,013,855 A | 1/2000 | McPherson et al. |
| 6,046,426 A | 4/2000 | Jeantette et al. |
| 6,049,054 A | 4/2000 | Panchison et al. |
| 6,087,553 A | 7/2000 | Cohen et al. |
| 6,096,043 A | 8/2000 | Techiera et al. |
| 6,128,866 A | 10/2000 | Wearne |
| 6,132,468 A | 10/2000 | Mansmann |
| 6,139,585 A | 10/2000 | Li |
| 6,164,032 A | 12/2000 | Beck |
| 6,171,340 B1 | 1/2001 | McDowell |
| 6,190,407 B1 | 2/2001 | Ogle et al. |
| 6,206,924 B1 | 3/2001 | Timm |
| 6,206,927 B1 | 3/2001 | Fell et al. |
| 6,215,093 B1 | 4/2001 | Meiners et al. |
| 6,248,131 B1 | 6/2001 | Felt et al. |
| 6,251,143 B1 | 6/2001 | Schwartz et al. |
| 6,261,322 B1 * | 7/2001 | Despres et al. ............ 623/23.53 |
| 6,280,478 B1 | 8/2001 | Richter et al. |
| 6,283,997 B1 | 9/2001 | Garg et al. |
| 6,299,645 B1 | 10/2001 | Ogden |
| 6,344,061 B1 | 2/2002 | Leitao et al. |
| 6,355,086 B2 | 3/2002 | Brown et al. |
| 6,370,382 B1 | 4/2002 | Kang et al. |
| 6,371,958 B1 | 4/2002 | Overaker |
| 6,385,585 B1 | 5/2002 | Jonsson et al. |
| 6,395,327 B1 | 5/2002 | Shetty |
| 6,406,497 B2 | 6/2002 | Takei |
| 6,415,574 B2 | 7/2002 | Beck |
| 6,454,811 B1 | 9/2002 | Sherwood et al. |
| 6,476,343 B2 | 11/2002 | Keicher et al. |
| 6,482,209 B1 | 11/2002 | Engh et al. |
| 6,494,914 B2 | 12/2002 | Brown et al. |
| 6,520,996 B1 | 2/2003 | Manasas et al. |
| 6,530,951 B1 | 3/2003 | Bates et al. |
| 6,551,608 B2 | 4/2003 | Yao |
| 6,558,421 B1 | 5/2003 | Fell et al. |
| 6,582,715 B1 | 6/2003 | Barry et al. |
| 6,589,283 B1 | 7/2003 | Metzger et al. |
| 6,592,598 B2 | 7/2003 | Vibe-Hansen et al. |
| 6,599,301 B2 | 7/2003 | Vibe-Hansen et al. |
| 6,610,067 B2 | 8/2003 | Tallarida et al. |
| 6,626,945 B2 | 9/2003 | Simon et al. |
| 6,632,246 B1 | 10/2003 | Simon et al. |
| 6,652,246 B1 | 11/2003 | Lin et al. |
| 6,652,587 B2 | 11/2003 | Felt et al. |
| 6,679,917 B2 | 1/2004 | Ek |
| 6,682,567 B1 | 1/2004 | Schroeder |
| 6,686,437 B2 | 2/2004 | Buchman et al. |
| 6,699,252 B2 | 3/2004 | Farr, II et al. |
| 6,709,462 B2 | 3/2004 | Hanssen |
| 6,712,822 B2 | 3/2004 | Re et al. |
| 6,712,856 B1 | 3/2004 | Carignan et al. |

| | | | | | |
|---|---|---|---|---|---|
| 6,716,957 B2 | 4/2004 | Tunc | 2007/0142914 A1 | 6/2007 | Jones et al. |
| 6,743,232 B2 | 6/2004 | Overaker et al. | 2007/0156249 A1 | 7/2007 | Lawrynowicz et al. |
| 6,770,099 B2 | 8/2004 | Andriacchi et al. | 2007/0225390 A1 | 9/2007 | Wang et al. |
| 6,846,329 B2 | 1/2005 | McMinn | 2008/0004709 A1 | 1/2008 | O'Neill et al. |
| 6,850,125 B2 | 2/2005 | Norman et al. | 2008/0050412 A1 | 2/2008 | Jones et al. |
| 6,852,125 B2 | 2/2005 | Simon et al. | 2008/0161927 A1 | 7/2008 | Savage et al. |
| 6,855,165 B2 | 2/2005 | Fell et al. | 2009/0068245 A1 | 3/2009 | Noble et al. |
| 6,863,689 B2 | 3/2005 | Ralph et al. | 2009/0087605 A1 | 4/2009 | Ramsey et al. |
| 6,866,684 B2 | 3/2005 | Fell et al. | | | |
| 6,893,463 B2 | 5/2005 | Fell et al. | | | |

FOREIGN PATENT DOCUMENTS

| | | | |
|---|---|---|---|
| DE | 19502733 A1 | 3/1996 |
| EP | 0 178 650 A2 | 4/1986 |
| EP | 0295038 A2 | 12/1988 |
| EP | 0 528 800 A1 | 3/1993 |
| EP | 0761242 A1 | 3/1997 |
| EP | 1 300 511 A2 | 4/2003 |
| EP | 1418013 A1 | 5/2004 |
| EP | 1426013 A1 | 6/2004 |
| EP | 1455666 A1 | 9/2004 |
| EP | 1493455 A2 | 1/2005 |
| EP | 1683593 A2 | 7/2006 |
| EP | 1806154 A1 | 7/2007 |
| EP | 1949989 A1 | 7/2008 |
| JP | 2255329 A | 10/1990 |
| JP | 4041794 A | 2/1992 |
| JP | 11287020 A | 10/1999 |
| JP | 2001303751 A | 10/2001 |
| RU | 2218242 C2 | 12/2003 |
| WO | 9606881 A2 | 3/1996 |
| WO | 2005/084216 A2 | 9/2005 |
| WO | 2005087982 A1 | 9/2005 |
| WO | 2007058160 A1 | 5/2007 |

Full US patent list continues:

6,911,044 B2 6/2005 Fell et al.
6,916,341 B2 7/2005 Rolston
6,921,264 B2 7/2005 Mayer et al.
6,923,831 B2 8/2005 Fell et al.
6,932,610 B2 8/2005 Ono et al.
7,168,283 B2 1/2007 Van Note et al.
7,494,507 B2 2/2009 Dixon et al.
7,674,517 B2 3/2010 Ramsey et al.
2001/0014403 A1 8/2001 Brown et al.
2002/0010512 A1 1/2002 Takei
2002/0015654 A1 2/2002 Das et al.
2002/0016635 A1 2/2002 Despres et al.
2002/0127328 A1 9/2002 Shetty
2002/0130112 A1 9/2002 Manasas et al.
2002/0151983 A1 10/2002 Shetty
2002/0173855 A1 11/2002 Mansmann
2002/0198528 A1 12/2002 Engh et al.
2003/0032351 A1 2/2003 Horner et al.
2003/0033018 A1 2/2003 Merchant
2003/0045941 A1 3/2003 Lewallen
2003/0055500 A1 3/2003 Fell et al.
2003/0055501 A1 3/2003 Fell et al.
2003/0060882 A1 3/2003 Fell et al.
2003/0060883 A1 3/2003 Fell et al.
2003/0060884 A1 3/2003 Fell et al.
2003/0060885 A1 3/2003 Fell et al.
2003/0060888 A1 3/2003 Fell et al.
2003/0069638 A1 4/2003 Barlow et al.
2003/0069718 A1 4/2003 Hollister et al.
2003/0153977 A1 8/2003 Suguro et al.
2003/0153981 A1 8/2003 Wang et al.
2003/0155686 A1 8/2003 Hawkins et al.
2003/0158606 A1 8/2003 Coon et al.
2003/0209305 A1 11/2003 Smith et al.
2003/0220696 A1 11/2003 Levine et al.
2004/0006393 A1 1/2004 Burkinshaw
2004/0009228 A1 1/2004 Tormala et al.
2004/0015170 A1 1/2004 Tallarida et al.
2004/0023586 A1 2/2004 Tilton
2004/0044414 A1 3/2004 Nowakowski
2004/0054416 A1 3/2004 Wyss et al.
2004/0059356 A1 3/2004 Gingras
2004/0098132 A1 5/2004 Andriacchi et al.
2004/0121110 A1 6/2004 Schmidt et al.
2004/0143339 A1 7/2004 Axelson et al.
2004/0148030 A1 7/2004 Ek
2004/0153163 A1 8/2004 Posner
2004/0162622 A1 8/2004 Simon et al.
2004/0167633 A1 8/2004 Wen et al.
2004/0191106 A1 9/2004 O'Neill et al.
2004/0199249 A1 10/2004 Fell
2004/0199250 A1 10/2004 Fell
2004/0204766 A1 10/2004 Siebel
2004/0230315 A1 11/2004 Ek
2004/0243237 A1 12/2004 Unwin et al.
2004/0267363 A1 12/2004 Fell et al.
2005/0033424 A1 2/2005 Fell
2005/0043816 A1 2/2005 Datta et al.
2005/0079200 A1 4/2005 Rathenow et al.
2005/0085918 A1 4/2005 Soffiati et al.
2005/0100578 A1 5/2005 Schmid et al.
2005/0123672 A1 6/2005 Justin et al.
2005/0154471 A1 7/2005 Aram et al.
2005/0170159 A1 8/2005 Ramsey et al.
2005/0171604 A1 8/2005 Michalow
2005/0177169 A1 8/2005 Fisher et al.
2005/0192672 A1 9/2005 Wyss et al.
2006/0045903 A1 3/2006 Kadiyala et al.
2006/0147332 A1 7/2006 Jones et al.

OTHER PUBLICATIONS

N.K Vail, L D Swain, W.C. Fox, T.B. Aufdlemorte, G. Lee, J.W. Barlow, "Materials for biomedical applications," Materials and Design, 20, 1999, pp. 123-132.*

R.H Morgan, A.J. Papworth, C. Sutcliffe, P. Fox, W. O'Neill, "High density net shape components by direct laser re-melting of single phase powders," Journal of Materials Science, 37, 2002, pp. 3093-3100.*

K. Harvey (producer), "Fast masters," Research Intelligence, a publication of The University of Liverpool, Issue 13, Jun. 2002, pp. 1-8.*

"Direct Generation of Metal Parts and Tools by Selective Laser Powder Remelting (SLPR)", W. Meiners, C. Over, K. Wissenbach, R. Poprawe, pp. 655-661, Date: Aug. 9-11, 1999.

Created and Designed by Shaman Gaspar, Maintained by Peter Fox, "Direct Laser Remelting", "Project Web Site", Using Lasers to Grow 3D object on Stainless Steel; The University of Liverpool 2002; http://mserc.liv.ac.uk/research/dlr/dlr_html.

Dr. Kerron Harvey, producer, Research Intelligence, The University of Liverpool, Issue 13, Jun. 2002.

H.J. Niu and I.T.H. Chang, "Selective Laser Sintering of Gas and Water Atomized High Speed Steel Powders," Scripta Materialia vol. 41, No. 1, (1999), pp. 25-30.

Hawley's Condensed Chemical Dictionary, 14th edition. John Wiley & Sons, 2002. Definition: sintering.

Hollander et al., Structural mechanical and in vitro characterization of individually structured Ti-Al-4V produces by direct layer forming, Biomaterials, pp. 1-9, 2005.

Patello-femoral Arthroplasty X-ray Results, Stryker Howmedica Osteonics, date not known.

R.H. Morgan, A.J. Papworth, C. Sutcliffe, P. Fox, W. O'Neill, "High density net shape components by direct laser re-melting of single phase powders," Journal of Materials Science, 37, (2002), pp. 3093-3100.

The Metals Handbook, Desk Edition, 2nd Edition, ASM International, 1998, p. 29.

Vureal et al., Plasma-sprayed oxide ceramics on steel substrates, Surface Coatings and Technology, 97 (1997) 347-354.

European Search Report and Written Opinion, EP05028133, dated May 11, 2010.

PCT/US2008/008955 International Search Report and Written Opinion mailed Dec. 2, 2008.

PCT/US2008/008955 International Preliminary Report on Patentability mailed Feb. 4, 2010.

Meiners W, Over C, Wissenbach K, Poprawe R., Direct generation of metal parts and tools by selective laser powder remelting (SLPR). Proceedings of SFF, Austin, Texas, Aug. 9-11, 1999.

C.K. Chua et al. Development of a Tissue Engineering Scaffold Structure Library for Rapid Prototyping. Parts 1 and 2, International Journal of Advanced Manufacturing Technology, (2003) vol. 21, pp. 291-312.

European Search Report and Written Opinion, EP10162970, dated Jun. 17, 2010.

European Search Report and Written Opinion, EP06127218, dated May 6, 2010.

* cited by examiner

FIG. 3

| METAL POWDER | MEAM OVERLAP (%) | -500 | | | | | | | | | -250 | | | | | | | |
|---|---|---|---|---|---|---|---|---|---|---|---|---|---|---|---|---|---|---|
| | LASER SCANNING SPEED (mm/s) | 100 | 120 | 140 | 160 | 180 | 200 | 220 | 240 | 260 | 100 | 120 | 140 | 160 | 180 | 200 | 220 | 240 |
| | SUBSTRATE | | | | | | | | | | | | | | | | | |
| CoCr | Ti ALLOY | | | | | | | | | | | | | | | | | |
| | CoCr | | | | | | | | | | | | | | | | | |
| | STAINLESS STEEL | ✓ | ✓ | ✓ | ✓ | ✓ | ✓ | ✓ | ✓ | ✓ | ✓ | ✓ | ✓ | ✓ | ✓ | ✓ | ✓ | ✓ |
| Nb | Ti ALLOY | | | | | | | | | | | | | | | | | |
| | CoCr | | | | | | | | | | | | | | | | | |
| | STAINLESS STEEL | | | | | | | | | | | | | | | | | |
| Ta | Ti ALLOY | | | | | | | | | | | | | | | | | |
| | CoCr | | | | | | | | | | | | | | | | | |
| Ti | Ti ALLOY | | | | | | | | | | | | | | | | | |
| | CoCr | | | | | | | | | | | | | | | | | |

| | MEAM OVERLAP (%) | -40 | | | | | | | | | 25 | | | | | | | |
|---|---|---|---|---|---|---|---|---|---|---|---|---|---|---|---|---|---|---|
| 0 | LASER SCANNING SPEED (mm/s) | 160 | 170 | 180 | 190 | 200 | 210 | 220 | 230 | 240 | 100 | 120 | 140 | 160 | 180 | 200 | 220 | 240 |
| | SUBSTRATE | | | | | | | | | | | | | | | | | |
| CoCr | Ti ALLOY | | | | | | | | | | ✓ | ✓ | ✓ | ✓ | ✓ | ✓ | ✓ | ✓ |
| | CoCr | | | | | | | | | | ✓ | ✓ | ✓ | ✓ | ✓ | ✓ | ✓ | ✓ |
| | STAINLESS STEEL | | | | | | | | | | ✓ | ✓ | ✓ | ✓ | ✓ | ✓ | ✓ | ✓ |
| Nb | Ti ALLOY | ✓ | ✓ | ✓ | ✓ | ✓ | ✓ | ✓ | ✓ | ✓ | | | | | | | | |
| | CoCr | ✓ | ✓ | ✓ | ✓ | ✓ | ✓ | ✓ | ✓ | ✓ | | | | | | | | |
| | STAINLESS STEEL | ✓ | ✓ | ✓ | ✓ | ✓ | ✓ | ✓ | ✓ | ✓ | | | | | | | | |
| Ta | Ti ALLOY | ✓ | ✓ | ✓ | ✓ | ✓ | ✓ | ✓ | ✓ | ✓ | | | | | | | | |
| | CoCr | ✓ | ✓ | ✓ | ✓ | ✓ | ✓ | ✓ | ✓ | ✓ | | | | | | | | |
| Ti | Ti ALLOY | ✓ | ✓ | ✓ | ✓ | ✓ | ✓ | ✓ | ✓ | ✓ | | | | | | | | |
| | CoCr | ✓ | ✓ | ✓ | ✓ | ✓ | ✓ | ✓ | ✓ | ✓ | | | | | | | | |

| | MEAM OVERLAP (%) | 50 | | | | | | | | | 50 | | | | | | | |
|---|---|---|---|---|---|---|---|---|---|---|---|---|---|---|---|---|---|---|
| 0 | LASER SCANNING SPEED (mm/s) | 100 | 120 | 140 | 160 | 180 | 200 | 220 | 240 | 260 | 280 | 300 | 320 | 340 | 360 | 380 | 400 | 420 |
| | SUBSTRATE | | | | | | | | | | | | | | | | | |
| CoCr | Ti ALLOY | | | | | | | | | | | | | | | | | |
| | CoCr | | | | | | | | | | | | | | | | | |
| | STAINLESS STEEL | ✓ | ✓ | ✓ | ✓ | ✓ | ✓ | ✓ | ✓ | ✓ | ✓ | ✓ | ✓ | ✓ | ✓ | ✓ | ✓ | ✓ |
| Nb | Ti ALLOY | | | | | | | | | | | | | | | | | |
| | CoCr | | | | | | | | | | | | | | | | | |
| | STAINLESS STEEL | ✓ | ✓ | ✓ | ✓ | ✓ | ✓ | ✓ | ✓ | ✓ | | | | | | | | |
| Ta | Ti ALLOY | | | | | | | | | | | | | | | | | |
| | CoCr | | | | | | | | | | | | | | | | | |
| Ti | Ti ALLOY | | | | | | | | | | | | | | | | | |
| | CoCr | | | | | | | | | | | | | | | | | |

LASER-PRODUCED POROUS SURFACE

CROSS REFERENCE TO RELATED APPLICATIONS

This application is a continuation of U.S. application Ser. No. 12/386,679, filed on Apr. 22, 2009, which is a continuation of U.S. application Ser. No. 10/704,270, filed on Nov. 7, 2003, now U.S. Pat. No. 7,537,664, which claims the benefit of U.S. Provisional Application No. 60/424,923 filed on Nov. 8, 2002, and U.S. Provisional Application No. 60/425,657 filed on Nov. 12, 2002, the disclosures of which are incorporated herein by reference.

BACKGROUND OF THE INVENTION

The present invention relates to a porous surface and a method for forming the same, which uses a directed energy beam to selectively remelt a powder to produce a part. In particular, this invention relates to a computer-aided laser apparatus, which sequentially remelts a plurality of powder layers to build the designed part in a layer-by-layer fashion. The present application is particularly directed toward a method of forming a porous and partially porous metallic structure.

DESCRIPTION OF THE RELEVANT ART

The field of free-form fabrication has seen many important recent advances in the fabrication of articles directly from computer controlled databases. These advances, many of which are in the field of rapid prototyping of articles such as prototype parts and mold dies, have greatly reduced the time and expense required to fabricate articles, particularly in contrast to conventional machining processes in which a block of material, such as a metal, is machined according to engineering drawings.

One example of a modern rapid prototyping technology is the selective laser sintering process practiced by systems available from DTM Corporation of Austin, Tex. According to this technology, articles are produced in layer-wise fashion from a laser-fusible powder that is dispensed one layer at a time. The powder is fused, remelted or sintered, by the application of laser energy that is directed in raster-scan fashion to portions of the powder layer corresponding to a cross section of the article. After the fusing of the powder in each layer, an additional layer of powder is dispensed, and the process repeated, with fused portions or lateral layers fusing so as to fuse portions of previous laid layers until the article is complete. Detailed descriptions of the selective laser sintering technology may be found in U.S. Pat. Nos. 4,863,538, 5,017,753, 5,076,869 and U.S. Pat. No. 4,944,817, all assigned to Board of Regents, the University of Texas. Quasi-porous structures have also been developed in the form of regular and irregular lattice arrangements in which individual elements (column and connecting cross-members) are constructed singularly from a pre-defined computer-aided design model of the external geometry and lattice structure. The selective laser remelting and sintering technologies have enabled the direct manufacture of solid or dense three-dimensional articles of high resolution and dimensional accuracy from a variety of materials including wax, metal powders with binders, polycarbonate, nylon, other plastics and composite materials, such as polymer-coated metals and ceramics.

The field of the rapid prototyping of parts has, in recent years, made large improvements in broadening high strain, high density, parts for use in the design and pilot production of many useful articles, including metal parts. These advances have permitted the selective laser remelting and sintering processes to now also be used in fabricating prototype tooling for injection molding, with expected tool life in access of ten thousand mold cycles. The technologies have also been applied to the direct fabrication of articles, such as molds, from metal powders without a binder. Examples of metal powder reportedly used in such direct fabrication include two-phase metal powders of the copper-tins, copper-solder (the solder being 70% led and 30% tin), and bronze-nickel systems. The metal articles formed in these ways have been quite dense, for example, having densities of up to 70% to 80% of fully dense (prior to any infiltration). Prior applications of this technology have strived to increase the density of the metal structures formed by the remelting or sintering processes. The field of rapid prototyping of parts has focused on providing high strength, high density, parts for use and design in production of many useful articles, including metal parts.

However, while the field of rapid prototyping has focused on increasing density of such three-dimensional structures, the field has not focused its attention on reducing the density of three-dimensional structures. Consequently, applications where porous and partially porous metallic structures, and more particularly metal porous structures with interconnected porosity, are advantageous for use have been ignored. It is an object of this invention to use a laser and powder metal to form pores in structures in which pores are irregular in size and have a controlled total porosity. It is a further object to produce porous tissue in growth surfaces with interconnected porosity with uniform pores and porosity.

BRIEF SUMMARY OF THE INVENTION

The present invention relates to a method for producing a three-dimensional porous structure particularly for use with tissue ingrowth. In one embodiment of the present invention, a layer of metallic powder is deposited onto a substrate or a build platform. Preferred metals for the powder include titanium, titanium alloys, stainless steel, cobalt chrome alloys, tantalum or niobium. A laser beam with predetermined settings scans the powder layer causing the powder to preferentially remelt and consequently solidify with a decreased density, resulting from an increase in porosity as compared to a solid metal. The range of the laser's power may be between 5 W and 1000 W. After the first layer of powder has been completed, successive offset layering and remelting are continued until the porous part has been successfully completed. In this embodiment, the benefit of the part formed is that that decreased density increases porosity thus enabling the part to be used for, among other things, tissue ingrowth.

In a second embodiment, the first layer of metallic powder is deposited onto a solid base or core and fused thereto. Preferred metals used for the core include titanium, titanium alloys, stainless steel, cobalt chrome alloys, tantalum and niobium. Successive powder layers of the same or different materials are once again added in a layer-by-layer fashion until the part is completed. This embodiment has the desired effect of providing a structure in which the porosity may be increased as the structure is built, resulting in a graded profile in which the mechanical properties will also be reduced outwards from the core. This will allow the formed part to be used for, among other things, medical implants and prosthesis, but yet still include a surface for tissue ingrowth.

The method of producing a three-dimensional porous tissue ingrowth structure may include depositing a first layer of a powder made from a metal selected from the group consisting of titanium, titanium alloys, stainless steel, cobalt chrome alloys, tantalum and niobium, onto a substrate. Followed by scanning a laser beam at least once over the first layer of powder. The laser beam having a power (P) in Joule per seconds with a scanning speed (v) in millimeters per second with a range between 80 and 400 mms. and a beam overlap (b) in millimeters of between 50% and −1200%. Such that the number calculated by the formula P/(b×v) lies between the range 0.3-8 J/mm².

At least one additional layer of powder is deposited and then the laser scanning steps for each successive layer are repeated until a desired web height is reached. In a second embodiment, during the step of repeating the laser scanning steps, at least one laser scan is carried out angled relative to another laser scan in order to develop an interconnecting or non-interconnecting porosity.

The thickness of the first layer and said successive layers of powder is between 5 μm-2000 μm. The laser can be applied either continuously or in a pulse manner, with the frequency of the pulse being in the range of approximately 1 KHz to 50 KHz. Preferably, the method is carried out under an inert atmosphere, more preferably specifically an Argon inert atmosphere.

In order to achieve a greater mechanical strength between the base or core and the first layer of powder a third metal may be used to act as an intermediate. The third metal would act as a bond coat between the core and first layer of powder. Additionally the core may be integral with the resultant porous ingrowth structure and impart additional physical properties to the overall construct. The core may also be detachable from the resultant porous surface buildup.

It is the object of the present invention to provide a method of fabricating porous and partially porous metallic structures with a known porosity for use in particularly but not exclusively hard or soft tissue interlock structures or medical prosthesis.

These and other objects are accomplished by a process of fabricating an article in which laser-directed techniques are used to produce a porous three-dimensional structure with interconnected porosity and predetermined pore density, pore size and pore-size distribution. The article is fabricated, in the example of remelting, by using a laser and varying either the power of the laser, the layer thickness of the powder, laser beam diameter, scanning speed of the laser or overlap of the beam. In fabricating a three-dimensional structure, the powder can be either applied to a solid base or not. The article is formed in layer-wise fashion until completion.

BRIEF DESCRIPTION OF THE DRAWINGS

Methods of forming the porous surface of the present invention can be performed in many ways and some embodiments will now be described by way of example and with reference to the accompanying drawings in which:

FIG. 3 is a table showing a series of parameters used for the samples of FIG. 2;

DETAILED DESCRIPTION

Figure 1:
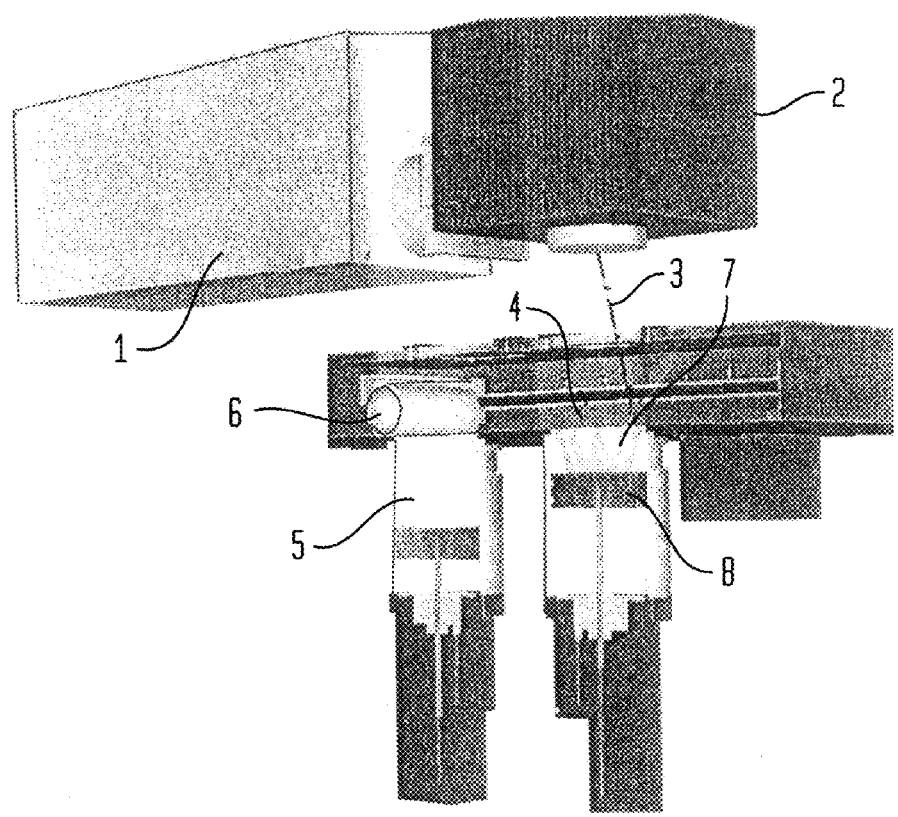
FIG. 1 is a diagrammatic illustration of the apparatus used to make test samples according to the processes of the present invention.

The present invention relates to a method of forming porous and partially porous metallic structures which are particularly but not exclusively applicable for use in hard or soft tissue interlock structures for medical implants and prosthesis. The method makes use of laser technology by employing a variety of scanning strategies. Typical metal and metal alloys employed include stainless steel, cobalt chromium alloys, titanium and its alloys, tantalum and niobium, all of which have been used in medical device applications. The present invention can be used for such medical device applications where bone and soft tissue interlock with a component is required, or where a controlled structure is required to more closely match the mechanical properties of the device with surrounding tissue. Additionally, the present invention may be employed to enhance the biocompatibility of a porous structure with animal tissue. With these advantages in mind, a structure may be created using specific dimensions required to accommodate a particular patient.

One particular intention of the present invention is to produce a three-dimensional structure using a direct laser remelt process, for example, for building structures with or without a solid base or core. When applied to an orthopedic prosthesis, the three-dimensional structure could be used to provide a porous outer layer to form a bone in-growth structure. Alternatively, the porous structure, when applied to a core, could be used to form a prosthesis with a defined stiffness to both fulfill the requirement of a modulus match with surrounding tissue and provide interconnected porosity for tissue interlock. A further use could be to form an all-porous structure with grade pore size to interact with more than one type of tissue. Again, the process can be used to build on a solid base or core with an outer porous surface, the porosity of which is constant or which varies. The base or core materials to which the process is applied is either titanium and its alloys, stainless steel, cobalt chrome alloys, tantalum or niobium. The preferred surface coatings are titanium, cobalt chrome and tantalum but both stainless steel and niobium can also be used. Fully porous structures may be built from any of the materials tested, with the preferred material being titanium. One intention of the present invention is to produce a method which can be exploited on a commercial basis for the production of, for example, bone interlock surfaces on a device although it has many other uses.

According to the present invention, a method of forming a three-dimensional structure includes building the shape by laser melting powdered titanium and titanium alloys, stainless steel, cobalt chrome alloys, tantalum or niobium. The laser may be a continuous wave or pulsed laser beam.

The method can be performed so that the structure is porous and if desired, the pores can be interconnecting to provide an interconnected porosity.

If desired, the method can include using a base or core of cobalt chrome alloy, titanium or alloy, stainless steel, niobium and tantalum, on which to build a porous layer of any one of the aforementioned metals and alloys by laser melting using a continuous or pulsed laser beam. Thus, a mixture of desired mixed materials may be employed.

Thus, the method can be applied to an existing article made from cobalt chrome, titanium or titanium alloys, stainless steel, tantalum or niobium, such as an orthopedic implant, to produce a porous outer layer from any of the aforementioned metals or alloys to provide a bone in-growth structure.

Preferably, prior to the deposition of any powder onto a substrate, a cleaning operation to ensure a contaminant-free surface may be employed. Typically, this process may include a solvent wash followed by a cleaning scan of the laser beam without the presence of particles.

In order to increase the mechanical bond between a substrate i.e., core or base, and a first layer of deposited powder a coating process may be employed. The coating process includes applying a third metal directly to the substrate, which has a higher bond strength to the substrate then does the first layer of powder. This process is particularly useful when the substrate and first powder layer are of different materials. The process of coating the substrate may be accomplished using known processes including laser deposition, plasma coating, cold gas dynamic spraying or similar techniques. One example of the coating process includes using either niobium or tantalum as an interface between a cobalt chrome alloy substrate and a first layer of titanium powder.

The present invention can also include a laser melting process, which precludes the requirement for subsequent heat treatment of the structure, thereby preserving the initial mechanical properties of the core or base metal.

The present invention may be applied to produce an all-porous structure using any of the aforementioned metal or metal alloys. Such structures can be used as finished product or further processed to form a useful device for either bone or soft tissue in-growth. Additionally, the structure may be used to serve some other function such as that of a lattice to carry cells.

The pore density, pore size and pore size distribution can be controlled from one location on the structure to another. It is important to note that successive powder layers can differ in porosity by varying factors used for laser scanning powder layers. As for example, a first layer of powder is placed and subsequently scanned. Next a second layer of powder is placed and scanned. In order to control porosity the second scan may be angled relative to the first scan. Additionally, the angling of the scanning as compared to previous and post scans may be maneuvered and changed many times during the process of building a porous structure. If a structure was built without alternating the angling of any subsequent scans you would produce a structure having a plurality of walls rather than one with an interconnecting or non-interconnecting porosity.

In one such method, the laser melting process includes scanning the laser beam onto the powder in parallel scan lines with a beam overlap i.e., scan spacing, followed by similar additional scans or subsequent scans at 90°. The type of scan chosen may depend on the initial layer thickness as well as the web height required. Web height refers to the height of a single stage of the porous structure. The web height may be increased by deposited additional layers of powder of a structure and scanning the laser at the same angle of the previous scan.

Further, the additional scan lines may be at any angle to the first scan, to form a structure with the formation of a defined porosity, which may be regular or random. The scan device may be programmed to proceed in a random generated manner to produce an irregular porous construct but with a defined level of porosity. Furthermore, the scan can be pre-programmed using digitized images of various structures, such as a trabecular bone, to produce a similar structure. Contrastingly, the scan may be pre-programmed using the inverse of digitized images, such as the inverse of a digitized trabecular bone to produce trabecular shaped voids. Many other scanning strategies are possible, such as a waffle scan, all of which can have interconnecting porosity if required.

The beam overlap or layer overlap may be achieved by rotation of the laser beam, the part being produced, or a combination of both.

A first method according to the present invention is intended to produce a porous structure for bone in-growth on the outer surface layer of a prosthesis.

To produce a porous surface structure, the nature of the material formed as a result of laser melting of powdered beads is principally dependent on the thermal profile involved (heating rate, soaking time, cooling rate); the condition of the raw material (size and size distribution of powder particles); atmospheric conditions (reducing, inert or oxidizing chamber gas); and accurate control of the deposited layer thickness.

There have been a number of studies to determine the optimum pore structure for maximization of bone in-growth on prostheses. The general findings suggest that optimum porosity is between approximately 20% and 40%, and aim to mid value with a mean volume percent of voids of about 70%. The preferred pore structure is irregular and interconnected, with a minimum pore size between about 80 μm and 100 μm and a maximum pore size between 80 μm and 800 μm. The structured thickness for in-growth is 1.4-1.6 mm, but can be larger or smaller depending on the application. As for example, it may be necessary to produce even smaller pore sizes for other types of tissue interaction or specific cellular interaction.

The first phase of development of the present invention involved an investigation, designed to characterize the material transformation process and to identify the optimum parameters for processing using three substrate materials CoCr and Ti stainless steel alloys, with five powder types Ti, CoCr, Ta and Nb, stainless steel.

The initial Direct Laser Remelting trials explored a comprehensive range of process parameters during the production of a number of coated base substrates. Results from this task were evaluated using laser scanning and white light interferometry in order to define the range of process parameters that produced the optimum pore structure.

Referring to FIG. 1, there is shown the apparatus used to carry out the method which comprises an Nd;YAG industrial laser 10 manufactured by Rofin Sinar Lasers, in Hamburg, Germany, integrated to an RSG1014 analogue galvo-scanning head 2 providing a maximum scan speed of 500 mm/s. The laser beam 3 is directed into an atmospherically controlled chamber 4, which consists of two computer-controlled platforms for powder delivery and part building. The powder is delivered from a variable capacity chamber 5 into the chamber 4 and is transported by a roller 6 to a build platform 7 above a variable capacity build chamber 8. In the embodiment shown in FIG. 1, the build and delivery system parameters are optimized for an even 100 μm coating of powder to be deposited for every build layer. The metals chosen as surface materials are all difficult to process due to their affinity for oxygen. Cr and Ti are easily oxidized when processed by laser in oxygen-containing atmosphere, their oxide products have high melting points and poor flowability. For this reason, and to prevent the formation of other undesirable phases, the methods were carried out under an Argon inert atmosphere in chamber 16. Pressure remained at or below atmospheric pressure during the entire application.

The build chamber 24 illustrated in FIG. 1 and method of layering described above is suitable for test specimens and constructs such as three-dimensional freestanding structures. However, in order to build on to an existing device, such as acetabular metal shells, hip and knee femoral components, knee tibial components and other such devices, considerable changes to the powder laying technique would need to be applied.

Preliminary experiments were performed on CoCr alloy to determine the efficacy of in-situ laser cleaning of the substrate. Typical processing conditions were: Laser power of 82 W, pulse frequency of 30 KHz, and a laser scan speed of 160 mm/sec.

Preliminary experiments were performed on CoCr to assess the environment conditions within the chamber. In these examples, Co212-e Cobalt Chrome alloy was used. The CoCr was configured into square structures, called coupons. Arrays of CoCr coupons were built onto a stainless steel substrate. The Co212-e Cobalt Chrome alloy had a particle size distribution of 90<22 um, i.e., 90% of the particles are less than 22 μm, the composition of which is shown in the table below.

TABLE 1

Composition of Co212-e CoCr alloy

| Element | Cr | Mo | Si | Fe | Mn | Ni | N | C | Co |
|---------|------|-----|------|------|------|------|------|-------|---------|
| Wt % | 27.1 | 5.9 | 0.84 | 0.55 | 0.21 | 0.20 | 0.16 | 0.050 | Balance |

Figure 2:
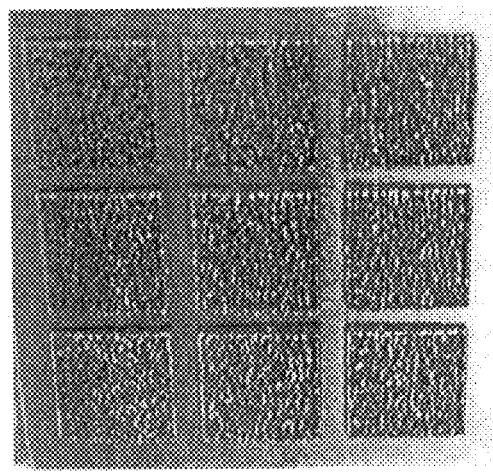
FIG. 2 is a photographic image showing an array of samples produced by the processes as performed by the apparatus of FIG. 1.

An array of nine sample coupons were produced as shown in FIG. 2, with the process of Table 2, using a maximum laser power of 78 watts (W) and laser scanning speed for each coupon varying between 100-260 mms$^{-1}$. Of course a higher laser power may be employed; however, a higher laser power would also necessitate increasing the speed of the laser scan speed in order to produce the desired melting of the powder layer. A simple linear x-direction scan was used on each of the coupons. This allowed the processing parameter, beam overlap, to be used to control the space between successive scan lines. That is, with a 100 μm laser spot size, an overlap of −200% produces a 100 μm gap between scans. Although the acceptable range for the beam overlap is given at +50% to −1200% it should be duly noted that the negative number only refers to the fact the there is a gap as opposed to a beam overlap between successive scans. For instance a beam overlap of zero refers to the fact that successive scans on the same layer of powder border each other. If the beam overlap was 5% then 5% of the first scan is overlapped by the second scan. When computing the Andrew number the absolute value of the beam overlap is used. The complete set of process parameters used is shown in Table 2 below.

TABLE 2

Process parameters

| Power Watts (W) | Layer Thickness (μm) | Beam Diameter (μm) | Scanning Speed (mms$^{-1}$) | Atmosphere | No. of Layers | Overlap (% of line width) |
|---|---|---|---|---|---|---|
| 78 | 100 | 100 | 100-260 | No | 16 | 25, 50, −500 |

The incremental changes in scanning speed and the size of the speed range were modified as the experiments progressed. To begin with, a large range of speeds was used to provide an initial indication of the material's performance and the propensity to melt. As the experiments progressed, the range was reduced to more closely define the process window. Speed and beam overlap variations were used to modify the specific energy density being applied to the powder bed and change the characteristics of the final structure. The complete series of parameters are given in FIG. 3, the parameters sets used for the definitive samples are shaded in gray.

CoCr was the first of four powders to be examined and, therefore, a wide range of process parameters was used. In each case, laser power and the pulse repetition rate were kept constant, i.e., continuous laser pulse, to allow the two remaining parameters to be compared. Layer thickness was maintained at 100 μm throughout all the experiments described here. Layer thickness can, however, vary between 5 μm to 2000 μm.

On completion of the initial series of experiments using CoCr powder on 2.5 mm thick stainless steel substrates, basic optical analysis was conducted of the surface of the coupons to ascertain the size of the pores and degree of porosity being obtained. Once a desired pore size was obtained and the coupons had suitable cohesion, the two experiments closest to the optimum desired pore size were repeated using first CoCr and then Ti substrates. The same structure could be obtained by other parameters.

Following the conclusion of the CoCr experiments, the remaining three powders; Niobium, Tantalum and Titanium were investigated in turn. The procedure followed a simple course although fewer parameter sets were explored as the higher melting points of these materials forced the reduction in speeds compared to CoCr powder.

For Niobium, the particle size description was 80%<75 μm at a purity of 99.85%. Due to its higher melting temperature compared to that of CoCr (Nb being at about 2468° C., and CoCr being at about 1383° C.), the laser parameters used included a reduced scanning speed range and increased beam overlap providing increased specific energy density at the powder bed. In addition, the pulse repetition rate was varied from 20 kHz to 50 kHz.

On completion of a small number (four in total) of preliminary experiments of Nb on stainless steel substrate, the experiment with the most ideal parameters was repeated on both the CoCr and Ti substrates.

The Tantalum used in this study had a particular size distribution of 80%<75 μm with a purity of 99.85%. Ta has a melting point of about 2996° C. and was processed using the same laser parameters as Nb. Now confident of the atmospheric inertness, the Ta powder was melted directly onto the CoCr and Ti substrates.

Bio-medical alloys of Titanium were not readily available in powder form and so pure Ti was chosen. The particle size distribution for the Ti powder was 80%<45 μm with a purity of 99.58%. The same parameters used for Nb and Ta were also used for the Ti powder. Ti has a lower melting point than Ta or Nb, Ti being at about 1660° C., but has a higher thermal conductivity than Ta or Nb. This implies that although the powder should require less energy before melting, the improved heat transfer means a larger portion of the energy is conducted away from the melt pool.

Following the completion of samples with all four powders on the required substrates, surface analysis was conducted using optical analysis and a scanning electron microscope to obtain images of the resultant pores. Porosity was calculated using a simple image processing technique involving the setting of contrast thresholds and pixel counting. While this technique is not the most accurate method, it allows the rapid analysis of small samples produced. Techniques such as Xylene impregnation would yield more accurate results but they are time consuming and require larger samples than those produced here.

Following an extended series of experimentation, two sets of laser processing parameters were selected for the laser melting of CoCr powder. From analysis of the stainless steel substrates, it was seen that a large portion of the results fell within the pore size required for these materials, stated as being in the range of 80 μm to 400 μm.

Optical analysis of the surface structure of each of the coupons produced with CoCr on CoCr and Ti alloy substrates were initially viewed but due to problems with the depth of field associated with an optical microscope, little information could be extracted. In addition to the coupons that were produced to satisfy the project requirements, two experiments were conducted using a relatively large negative beam overlap of −250 and −500%. Optical images of the coupon's surface and in section are shown in FIG. 4. These were not the definitive parameters chosen for the final arrays on CoCr and Ti alloy substrates as the pore size exceeds the required 80 μm to 400 μm. They are shown here to display what the Direct Laser Remelting process can produce when an excessive beam overlap is used.

Figure 5A:
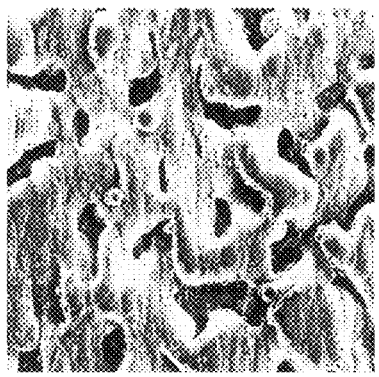
Figure 5B:
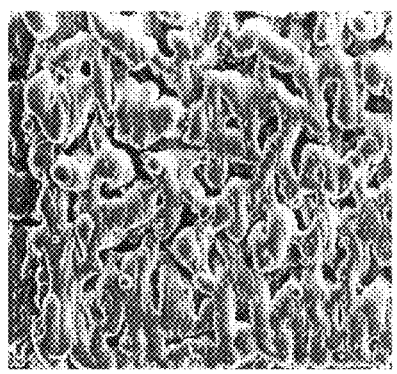
Figure 6A:
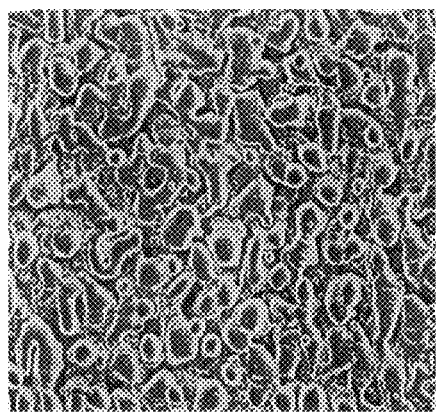
Figure 6B:
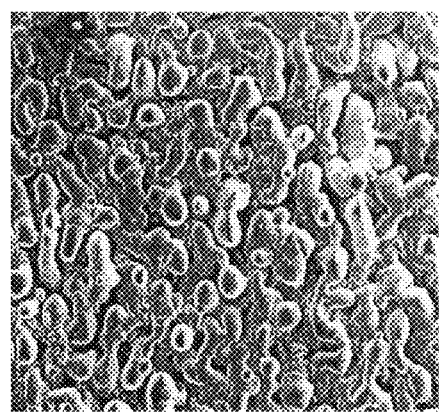
Figure 6C:
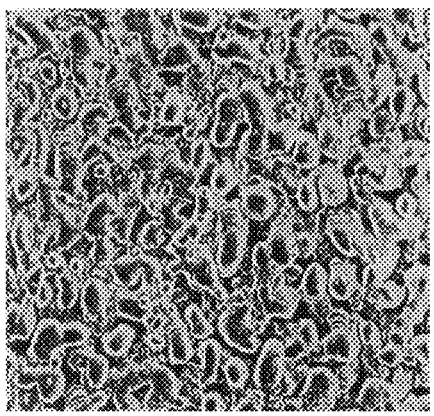
Figure 6D:
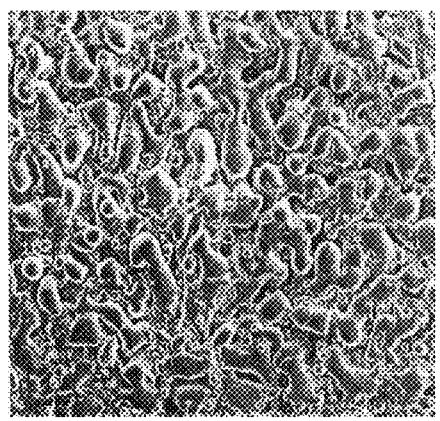
Figure 6E:
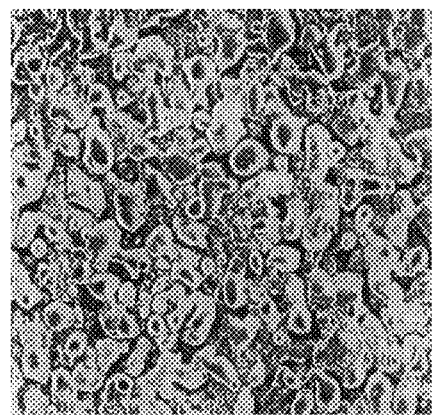

To provide a clearer indication of the pore size and pore density, the optical analysis was repeated using images obtained from the scanning electron microscope. FIG. 5 is an image of two coupons produced from a CoCr array on Ti alloy substrates. This array was chosen because it best satisfied the requirements of this exercise. The parameters were: laser power of 82 W continuous wave (cw); 25% beam overlap; scanning speed varied from 100 mms$^{-1}$ to 260 mms$^{-1}$ in 20 mm$^{-1}$ increments; the images of the coupons shown here, taken from this array, were produced with scanning speeds of 180 mms$^{-1}$ to 200 mms$^{-1}$. The surface is comprised of fused pathways that develop a network of interconnected pores. This structure continues throughout the layer until the interface is reached. The interface is characterized by a patchwork of fusion bonds. These bond sites are responsible for securing the interconnected surface structure to the baseplate. The macroscopic structure is covered with unmelted powder particles that appear to be loosely attached. In addition, there are larger resolidified globules that may have limited bonding to the surface.

FIGS. 6 and 7 are the scanning electron microscope images produced from the Nb and Ta coupons on Ti alloy substrates. Specifically, FIGS. 6(a) to 6(e) are scanning election microscope images of the surface structure of Nb on Ti alloy substrates, produced with a laser power of 82 W cw, −40% beam overlap. The scanning speeds used were: 160 mms$^{-1}$ for FIG. 6(a), 190 mms$^{-1}$ for FIG. 6(b), 200 mms$^{-1}$ for FIG. 6(c), 210 mms$^{-1}$ for FIG. 6(d) and 240 mms$^{-1}$ for FIG. 6(e), respectively.

Figure 7A:
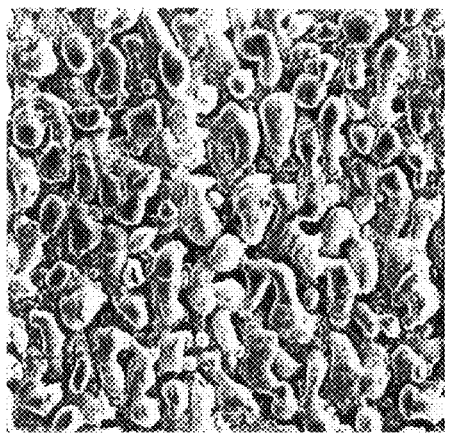
Figure 7B:
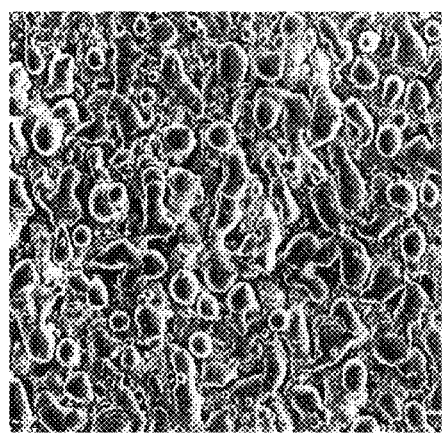
Figure 7C:
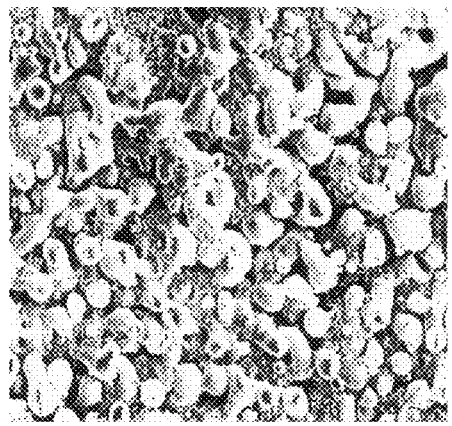
Figure 8A:
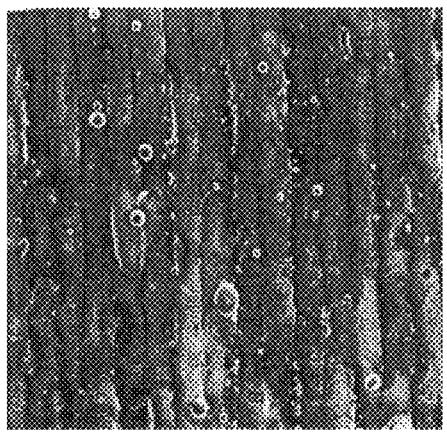
Figure 8B:
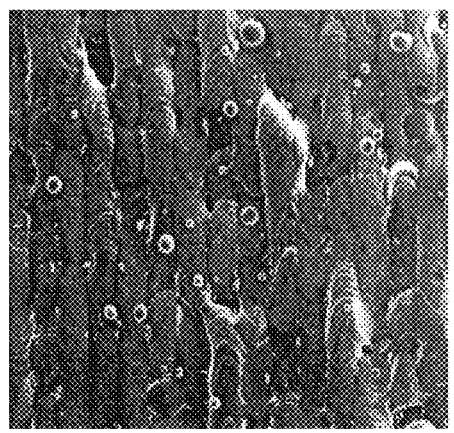
Figure 8C:
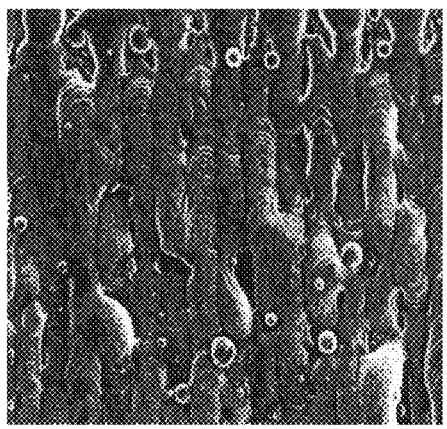
Figure 8D:
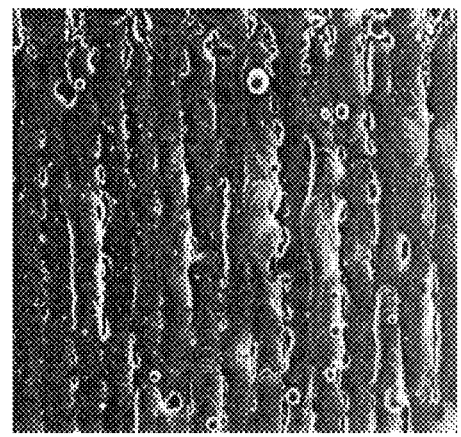
Figure 8E:
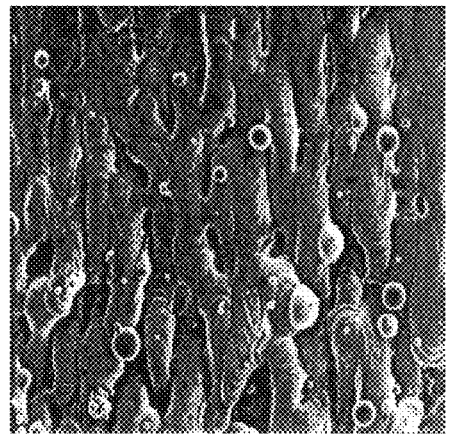
Figure 9A:
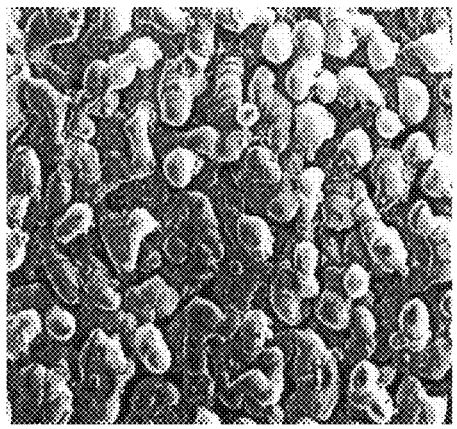
Figure 9B:
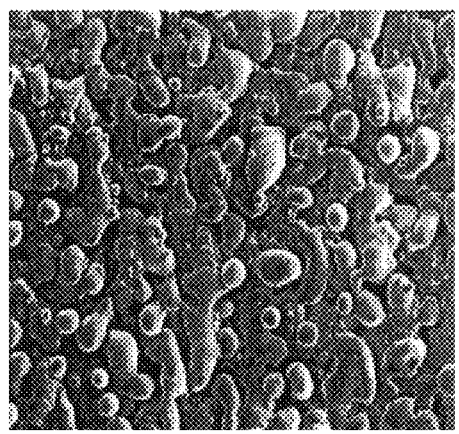
Figure 9C:
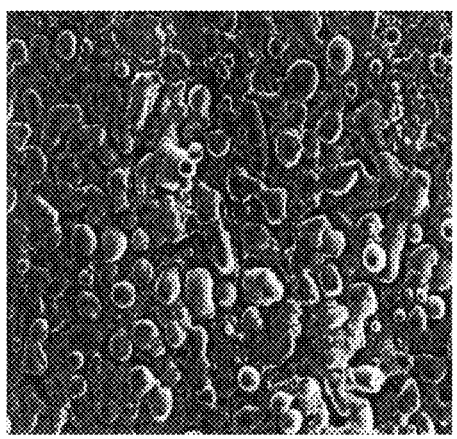
Figure 9D:
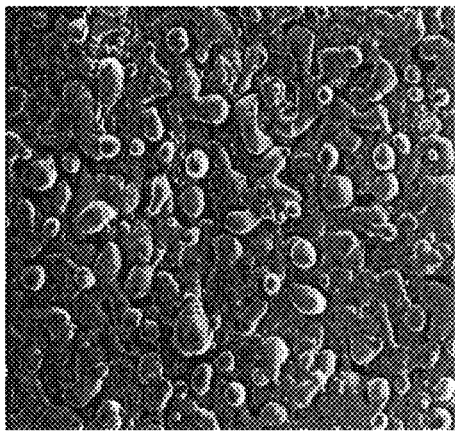
Figure 9E:
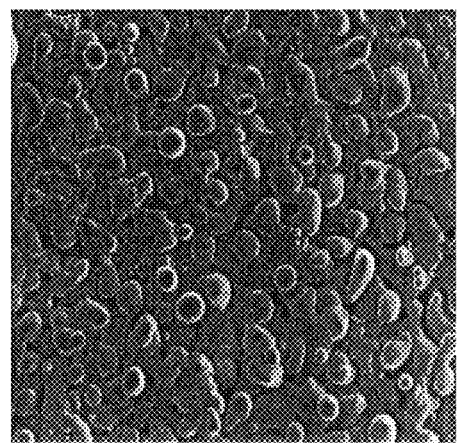
Figure 10A:
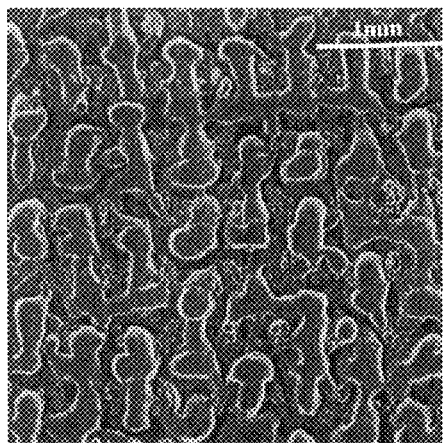
Figure 10B:
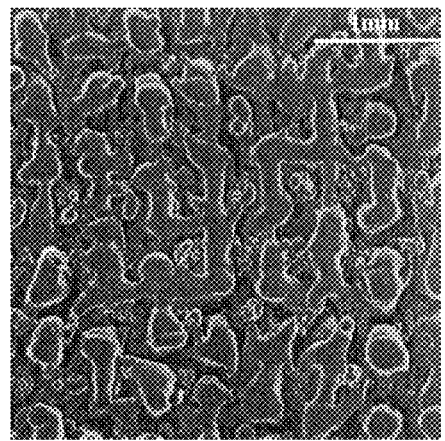
Figure 10C:
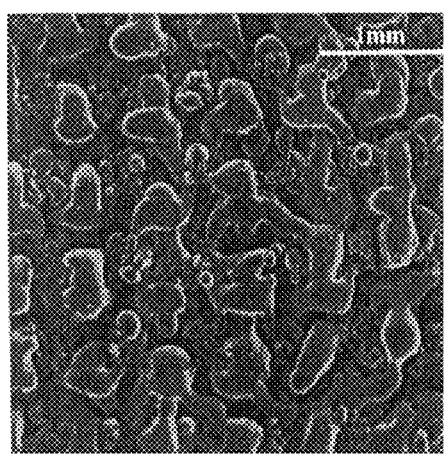
Figure 10D:
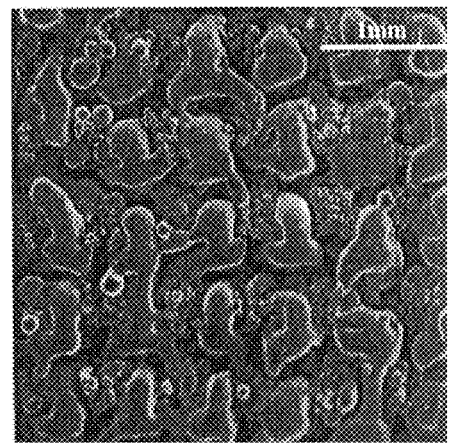
Figure 10E:
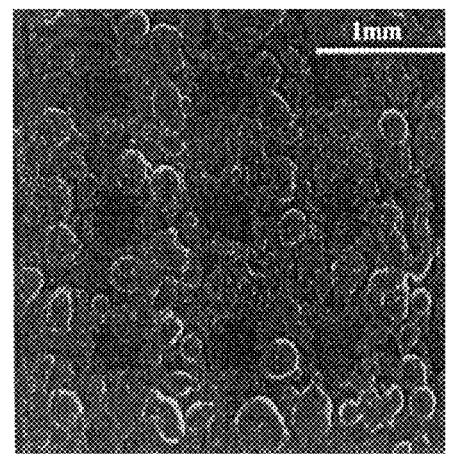
Figure 10F:
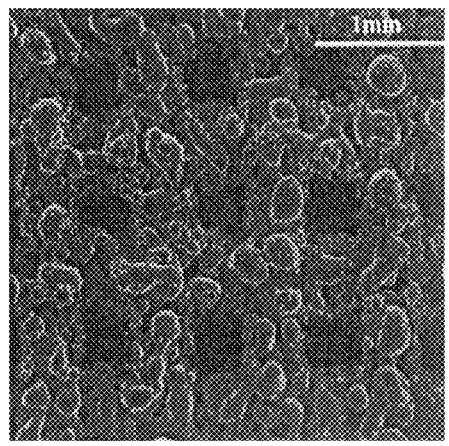

FIGS. 7(a) to 7(c) are scanning election microscope images of the surface structure of Ta on Ti alloy substrates produced using the same parameters used in the Nb or Ti alloy substrates except: FIG. 7(a) was produced with a scanning speed of 160 mms$^{-1}$; FIG. 7(b)'s speed was 200 mms$^{-1}$ and FIG. 7(c)'s speed was 240 mms$^{-1}$, respectively. An increased beam overlap was used here as Nb and Ta have high melting points, which require a greater energy density. The surfaces once again exhibit significant levels of unmelted powder particles and loosely attached resolidified beads that vary in size from a few microns to several hundred microns. All samples were loosely brushed after completion and cleaned in an ultrasonic aqueous bath. It is possible that further cleaning measures may reduce the fraction of loose particles.

FIGS. 8(a) to 8(e) are scanning electron microscope images taken from the Ti coupons on the CoCr alloy substrates. The laser processing parameters used were the same as those for the Nb and Ta powders, with once again only the speed varying. The scanning speed was varied from 160 mms$^{-1}$ (FIG. 8(a)), 170 mms$^{-1}$ (FIG. 8(b)), 200 mms$^{-1}$ (FIG. 8(c)); 230 mms$^{-1}$ (FIG. 8(d) to 240 mms$^{-1}$ (FIG. 8(e)). The Ti coupon on CoCr samples, (FIGS. 8(a) to 8(c)) indicate very high density levels compared to the other examples. The line-scans can be clearly seen, with good fusion between individual tracks, almost creating a complete surface layer. The surface begins to break up as the scanning speed is increased.

FIGS. 9(a) to 9(e) are scanning electron microscope images of surface structures of Ti on Ti alloy substrates produced with the same parameters used in FIGS. 8(a) to 8(e), respectively. It is unclear why Ti should wet so well on CoCr substrates. In comparison, Ti on Ti exhibits similar characteristic patterns as with Nb, Ta, and CoCr, specifically, an intricate network of interconnected pores.

Figure 11:
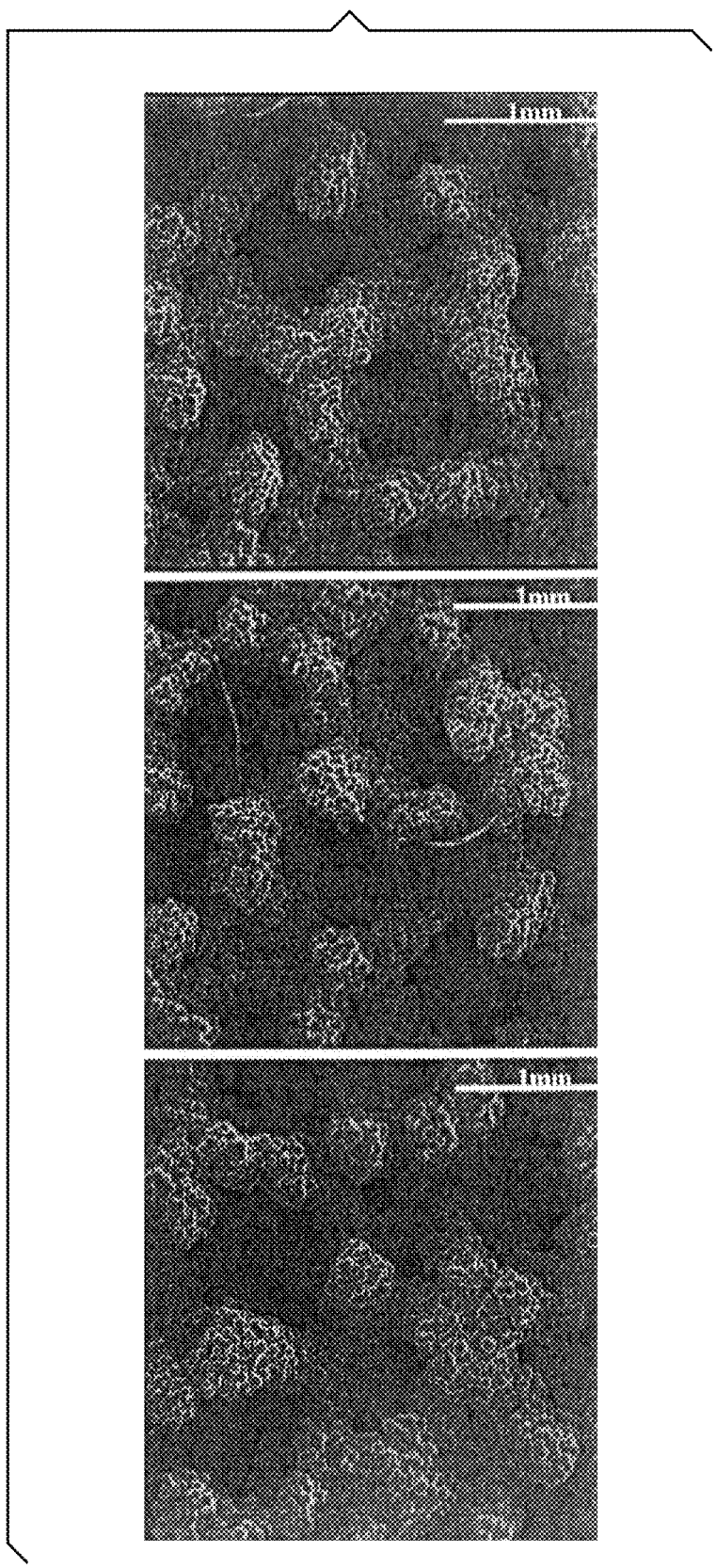
FIG. 11 is a scanning electron microscope micrograph taken from a porous Ti sintered structure.

Following the completion of the multi-layer coupons, a series of 20 mm×20 mm structures were produced from Ti that utilized an X and Y-direction "waffle" scanning format using the optimum Ti operating parameters with the two scans being orthogonal to one another. The intention behind these experiments was to demonstrate the ability of the Direct Laser Remelting process to produce parts with a controlled porosity, e.g. internal channels of dimensions equal to the required pore size, e.g. 80 μm to 400 μm. To do this, a relatively large beam overlap of between −400% and −600% was used. Scanning electron microscope images of the surfaces of these structures are shown in FIGS. 10(a) to 10(f). The scanning speed, 160 mms$^{-1}$ and the laser power 72 W cw were kept constant while the beam overlaps; −400% in FIGS. 10(a) and 10(b); −500% in FIGS. 10(c) and 10(d) and −600% in FIGS. 10(e) and 10(f), were varied accordingly. Scanning electron microscope micrographs, taken from a porous Ti sintered structure provided by Stryker-Howmedica are shown for reference in FIG. 11.

Figure 12:
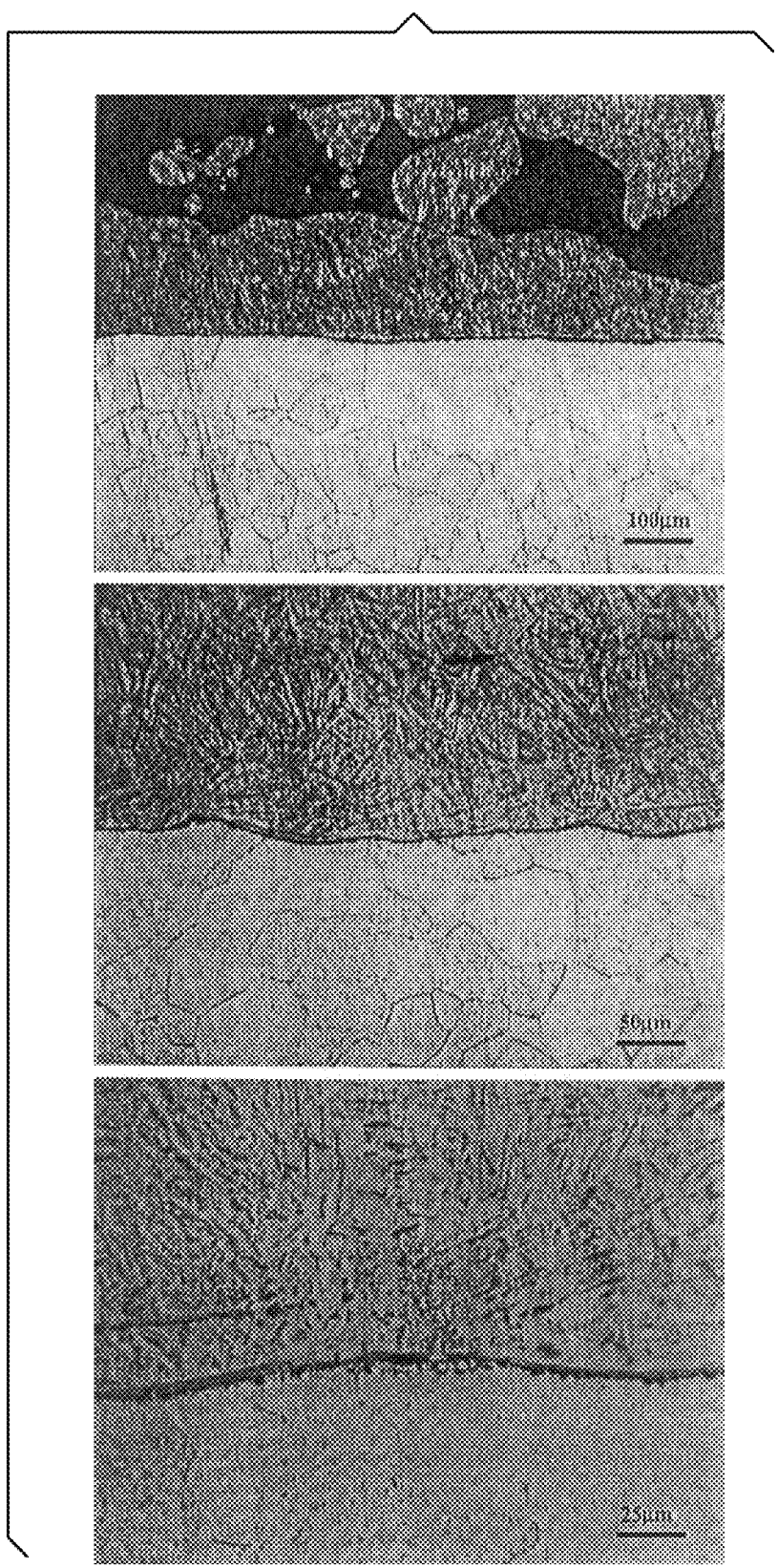
FIG. 12 is an optical image of a section through a sample showing the microstructure.

To illustrate more clearly the interaction between the substrate/structure metallurgical interaction, the Ti on Ti substrate was sectioned, hot mounted and polished using a process of 1200 and 2500 grade SiC, 6 μm diamond paste and 70/30 mixture of OPS and 30% $H_2O_2$. The polished sample was then etched with 100 ml $H_2O$, 5 ml NH.FHF and 2 cm$^3$ HCl for 30 seconds to bring out the microstructure. Optical images of this sample in section are shown in FIG. 12.

Figure 13:
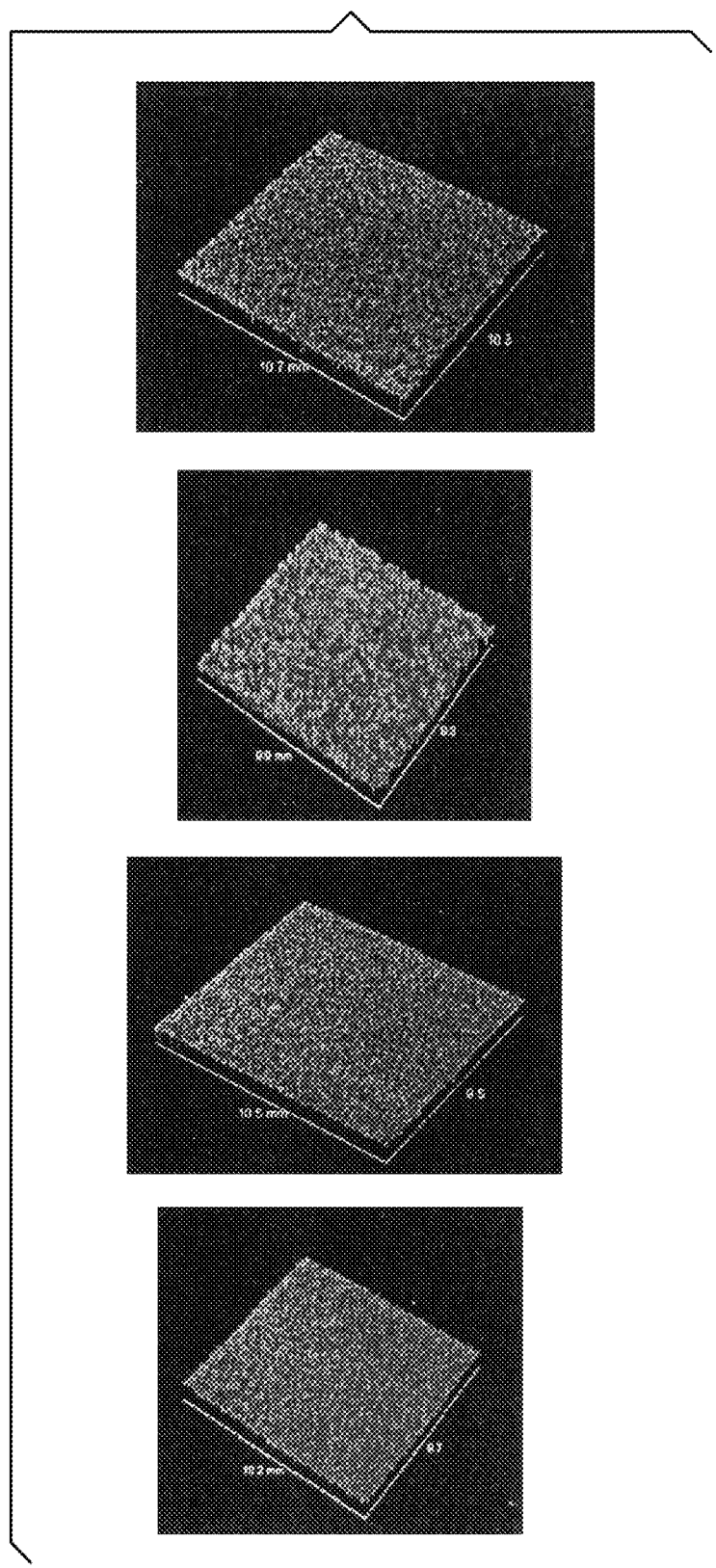
FIG. 13 is an image detailing surface structures.

FIG. 13 is an image taken from a non-contact surface profilimentry to show the surface structures obtained when using Ti, CoCr, Ta and Nb on Ti substrates. Values for Ra, Rq and Rb roughness are also shown.

From the optical and scanning election microscope analysis conducted, it is apparent that the Direct Laser Remelting process is capable of satisfying the requirements for pore characteristics, concerning maximum and minimum pore size, interconnectivity and pore density. From the initial visual analysis of the CoCr coupons, it was apparent from these and other examples, that subtle variations in pore structure and coverage could be controlled by scanning velocity and line spacing.

The key laser parameters varied for forming the three-dimensional metallic porous structures are: (a) Laser scanning speed (v.) in (mms$^{-1}$), which controls the rate at which the laser traverses the powder bed; (b) Laser power, P(W), which in conjunction with the laser spot size controls the intensity of the laser beam. The spot size was kept constant throughout the experiment; (c) Frequency, (Hz) or pulse repetition rate. This variable controls the number of laser pulses per second. A lower frequency delivers a higher peak power and vice versa.

The line width can be related to the laser scanning speed and the laser power to provide a measure of specific density, known as the "Andrew Number", where:

$$An = \frac{P}{b \times v} \, (\text{J/mm}^{-2})$$

Where P denotes the power of the laser, v is the laser scanning speed and b denotes beam width of the laser. The Andrew number is the basis for the calculation of the present invention. The Andrew number may also be calculated by substituting the line separation (d) for beam width (b). The two methods of calculating the Andrew number will result in different values being obtained. When using line separation (d) as a factor only on track of fused powder is considered, whereas when using the beam width (b) as a factor, two tracks of fused powder are considered as well as the relative influence of one track to the next. For this reason we have chosen to concern ourselves with the Andrew number using scan spacing as a calculating factor. It can thus be appreciated, that the closer these tracks are together the greater the influence they have on one another.

Additionally, the laser power may be varied between 5 W and 1000 W. Utilizing lower power may be necessary for small and intricate parts but would be economically inefficient for such coatings and structures described herein. It should be noted that the upper limit of laser power is restricted because of the availability of current laser technology. However, if a laser was produced having a power in excess of 1000 W, the scanning speed of the laser could be increased in order that an acceptable Andrew number is achieved. A spot size having a range between 5 um(fix) to 500 um(fix) is also possible. For the spot size to increase while still maintaining an acceptable Andrew number, either the laser power must be increased or the scanning speed decreased.

The above formula gives an indication of how the physical parameters can vary the quantity of energy absorbed by the powder bed. That is, if the melted powder has limited cohesion, e.g. insufficient melting, the parameters can be varied to concentrate the energy supply to the powder. High Andrew numbers result in reduced pore coverage and an increase in pore size due to the effects of increased melt volume and flow. Low Andrew numbers result in low melt volume, high pore density and small pores. Current satisfactory Andrew numbers are approximately 0.3 J/mm$^{-2}$ to 8 J/mm$^{-2}$ and are applicable to many alternative laser sources. It is possible to use a higher powered laser with increased scanning speed and obtain an Andrew number within the working range stated above.

Figure 4A:
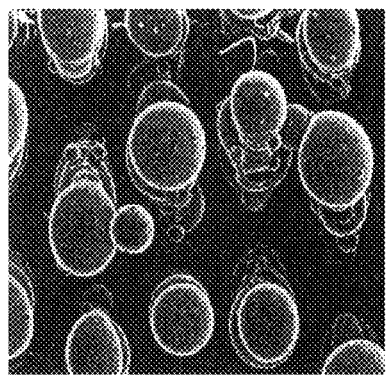
FIGS. 4 to 10 are scanning electron microscope images of the surface structure of various samples made by the method according to the invention.
Figure 4B:
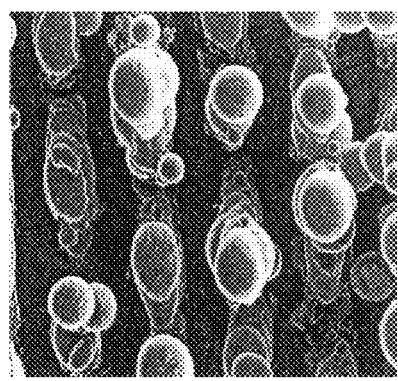
Figure 4C:
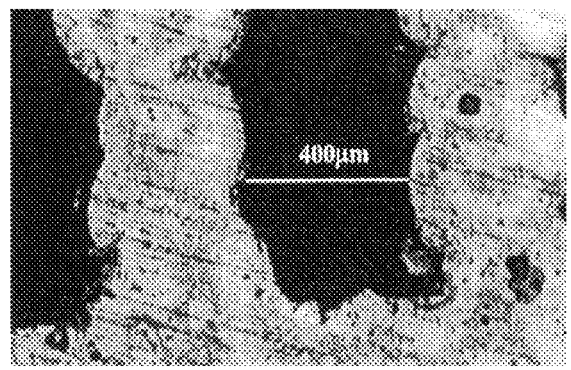

Line spacing or beam overlap can also be varied to allow for a gap between successive scan lines. It is, therefore, possible to heat selected areas. This gap would allow for a smaller or larger pore size to result. The best illustration of this is shown in FIGS. 4(a) to 4(c) where a −500% beam overlap has been applied. FIGS. 4(a) to 4(c) are scanning election microscope images of the surface structure of CoCr on stainless steel produced with a laser power of 82 W cw. FIG. 4(a) was produced with a laser scanning speed of 105 mms$^{-1}$ and FIG. 4(b) was produced with a laser scanning speed of 135 mms$^{-1}$. FIG. 4(c) is an image of the same structure in FIG. 4(b), in section. There is a significant self-ordering within the overall structure. Larger columnar structures are selectively built leaving large regions of unmelted powder. It is worth noting that these pillars are around 300 µm wide, over 1.6 mm tall and fuse well with the substrate, as seen in FIG. 4(c). Further analysis shows that the use of a hatched scanning format allows porosity to be more sufficiently controlled to allow the pore size to be directly controlled by the beam overlap.

The use of an optical inspection method to determine this approximate porosity is appropriate given the sample size. This method, although not accurate due to the filter selection process, can, if used carefully, provide an indication of porosity. An average porosity level of around 25% was predicted. This porosity level falls within the range of the desired porosity for bone in-growth structures. The mechanical characteristics of the porous structures are determined by the extent of porosity and the interconnecting webs. A balance of these variables is necessary to achieve the mechanical properties required by the intended application.

Increased fusion may, if required, be obtained by heating the substrate, powder or both prior to scanning. Such heating sources are commonly included in standard selective laser sintering/melting machines to permit this operation.

Following trials on the titanium build on the cobalt chromium substrate, it was determined that the interface strength was insufficient to serve the intended application. Trials were made by providing a bond coat of either tantalum or niobium on the cobalt chromium substrate prior to the deposition of the titanium layers to for the porous build. The typical protocol involved:

(i) Initial cleaning scan with a scan speed between 60 to 300 mm/sec, laser power 82 watts, frequency of 30 KHz, and a 50% beam overlap.

(ii) Niobium or tantalum deposition with three layers of 50 µm using a laser power of 82 watts, frequency 30 to 40 KHz, with a laser speed of between 160 to 300 mm/sec. The beam overlap was low at 50% to give good coverage.

(iii) A build of porous titanium was constructed using a laser power of 82 watts, frequency between 0 (cw) and 40 KHz, scanning speed of between 160 and 240 mm/sec, and beam overlap of −700%.

The strengths of the constructs are indicated in Table 3 with a comparison of the values obtained without the base coat.

TABLE 3

| SPECIMEN | MAXIMUM LOAD (kN) | TENSILE STRENGTH (MPa) | FAILURE MODE |
|---|---|---|---|
| Ti on CoCr | 2.5 | 5 | Interface |
| Ti on CoCr | 3.1 | 6.2 | Interface |
| 1 (Nb on Co—Cr) | 13.0 | 26.18 | 65% adhesive, 35% bond interface |
| 4 (Ti on Nb on Co—Cr) | 7.76 | 15.62 | Mostly bond coat interface |
| 5 (Ti on Nb on Co—Cr) | 9.24 | 18.53 | 20% adhesive, 40% bond coat, 40% porous Ti |
| 6 (Ti on Ta on Co—Cr) | 11.58 | 23.33 | Mostly adhesive with discrete webbing weakness |
| 8 (Ta on Co—Cr) | 13.93 | 27.92 | 60% adhesive, 40% bond interface |
| 9 (Ti on Ta on Co—Cr) | 6.76 | 13.62 | 100% bond interface |

Figure 26:
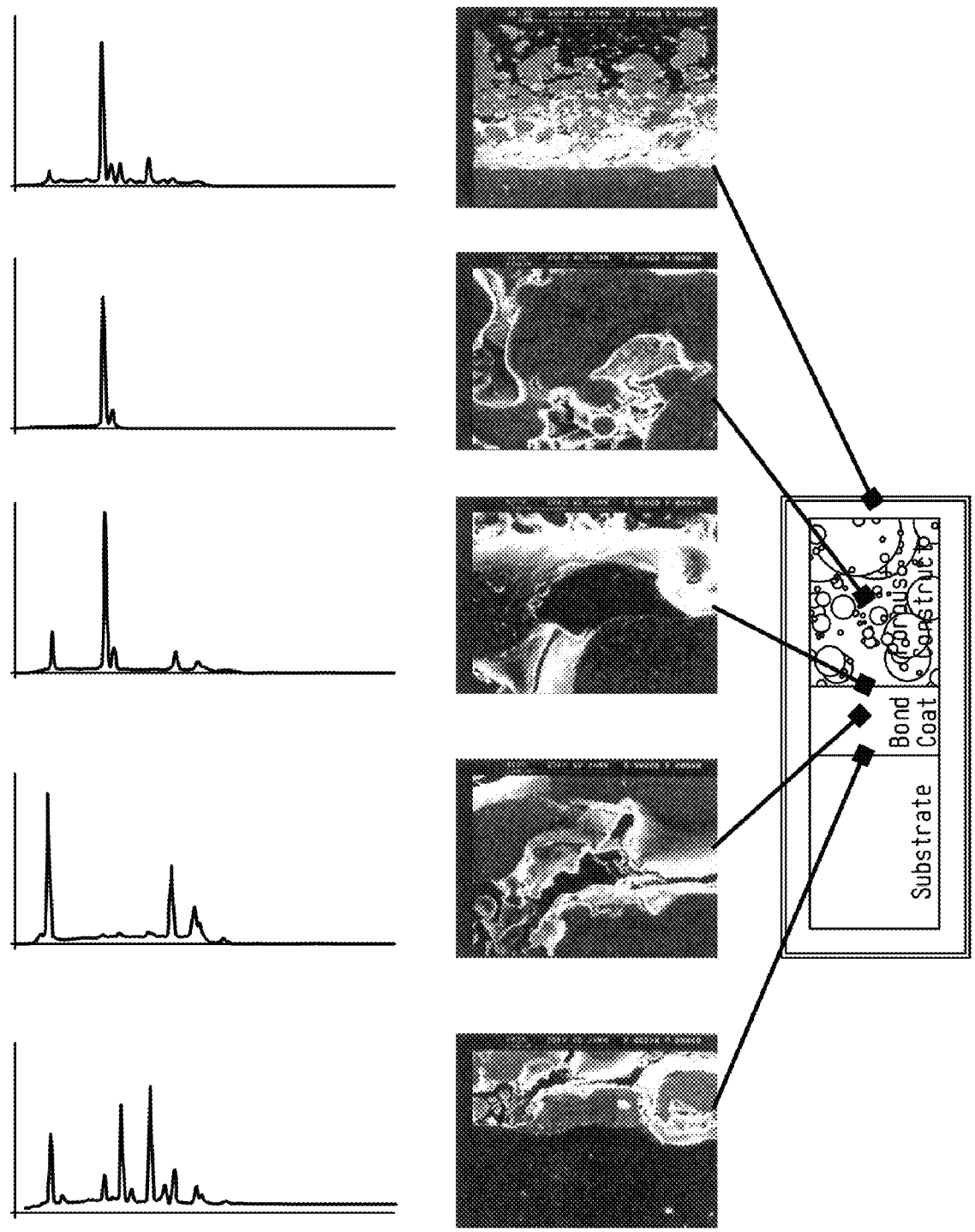
FIG. 26 indicates the metallography and spectra of a typical bond coat structure.

FIG. 26 shows the metallography of the structures with energy dispersive spectroscopy (EDS) revealing the relative metal positions within the build.

Figure 27:
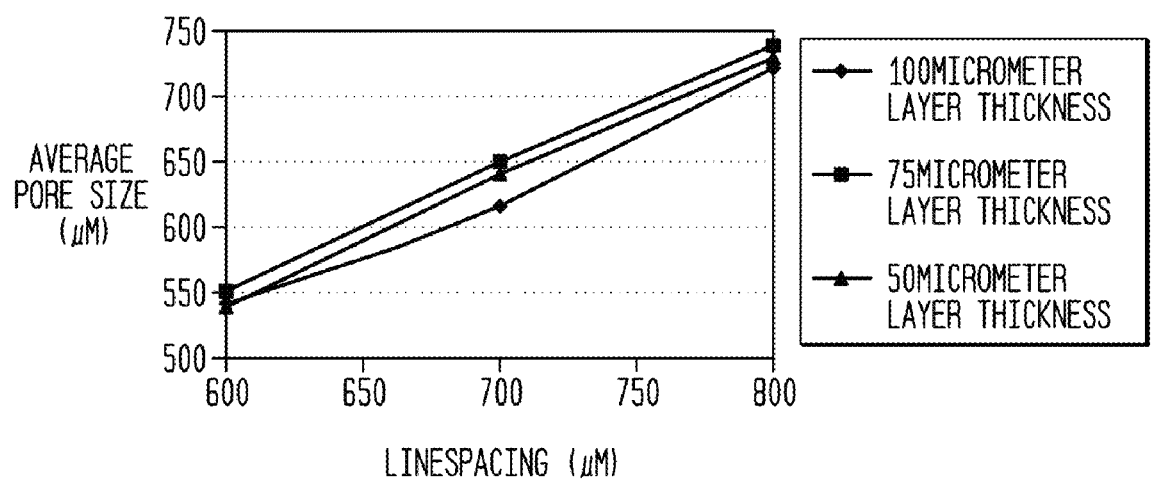
FIG. 27 shows the effect of line spacing on pore size.
Figure 28A:
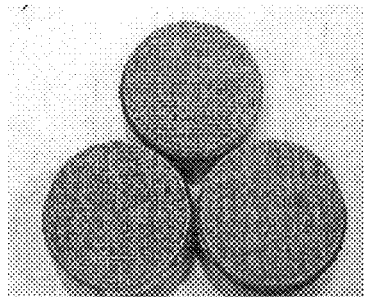
FIG. 28a-f are examples of typical waffle structures.
Figure 28B:
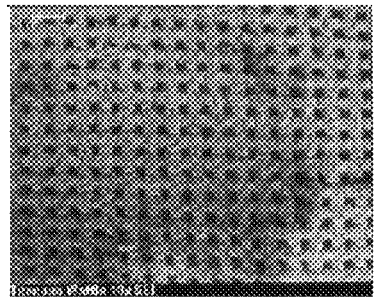
Figure 28C:
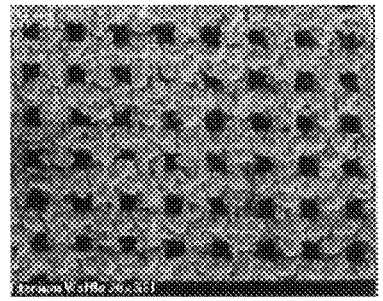
Figure 28D:
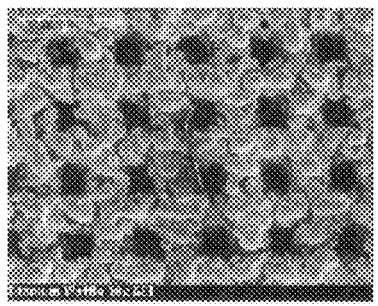
Figure 28E:
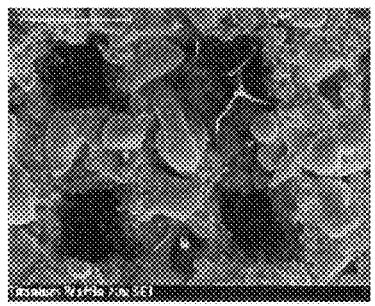
Figure 28F:
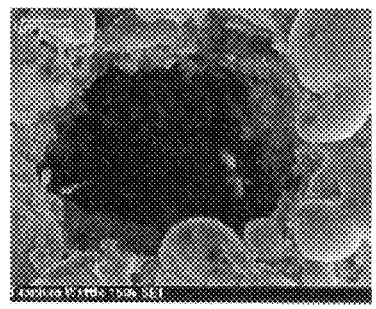

A typical waffle build of titanium on a titanium substrate was constructed as a way of regulating the porous structure. Scanning sequences of 0° 0° 0°, 90° 90° 90°, 45° 45° 45°, 135°,135°, 135°, of layer thickness 0.1 mm were developed to form a waffle. Three layers of each were necessary to obtain sufficient web thickness in the "z" direction to give a structure of adequate strength. Typical parameters employed were: Laser power was 82 watts, operating frequency between 0 (cw) and 40 KHz, scan speed of between 160 and 240 mm/sec with a beam overlap of −700%. FIG. 27 gives an indication of the effect of line spacing and pore size. FIG. 28 (*a*) shows typical examples of the waffle structure. The magnification level changes from 10, 20, 30, 70 and 150 times normal viewing as one moves respectively from FIG. (*b*) to (*f*). FIG. 28 (*a*) more specifically shows Ti powder on a Ti substrate with a controlled porosity by varying line spacing, i.e., beam overlap.

Figure 29:
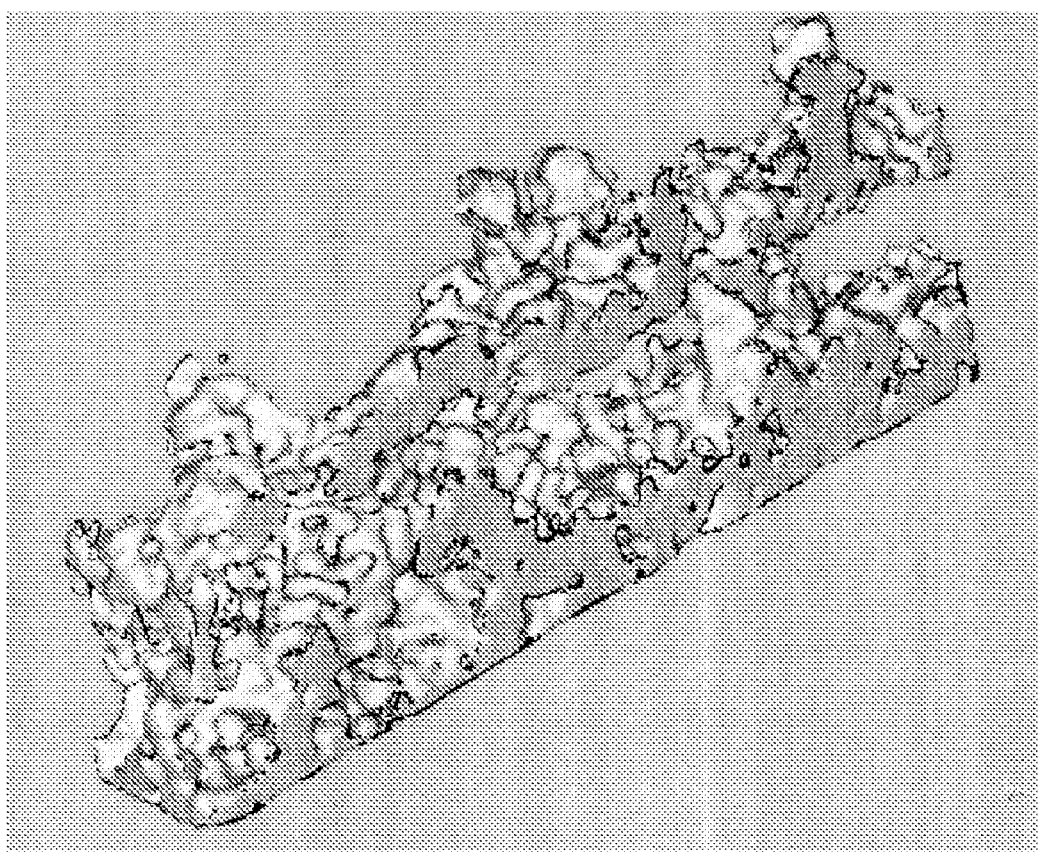
FIG. 29 is a trabecular bone-type structure constructed from a micro CT scan.

Trabecular structures of titanium on a titanium substrate were constructed as a way of randomising the porous structures. An STL (sterolithography) file representing trabecular structure was produced from a micro CT scan of trabecular bone. This file was sliced and the slice data sent digitally to the scanning control. This allowed the layer-by-layer building of a metallic facsimile to be realised. FIG. 29 shows a cross-sectional view of such a construct.

Figure 30:
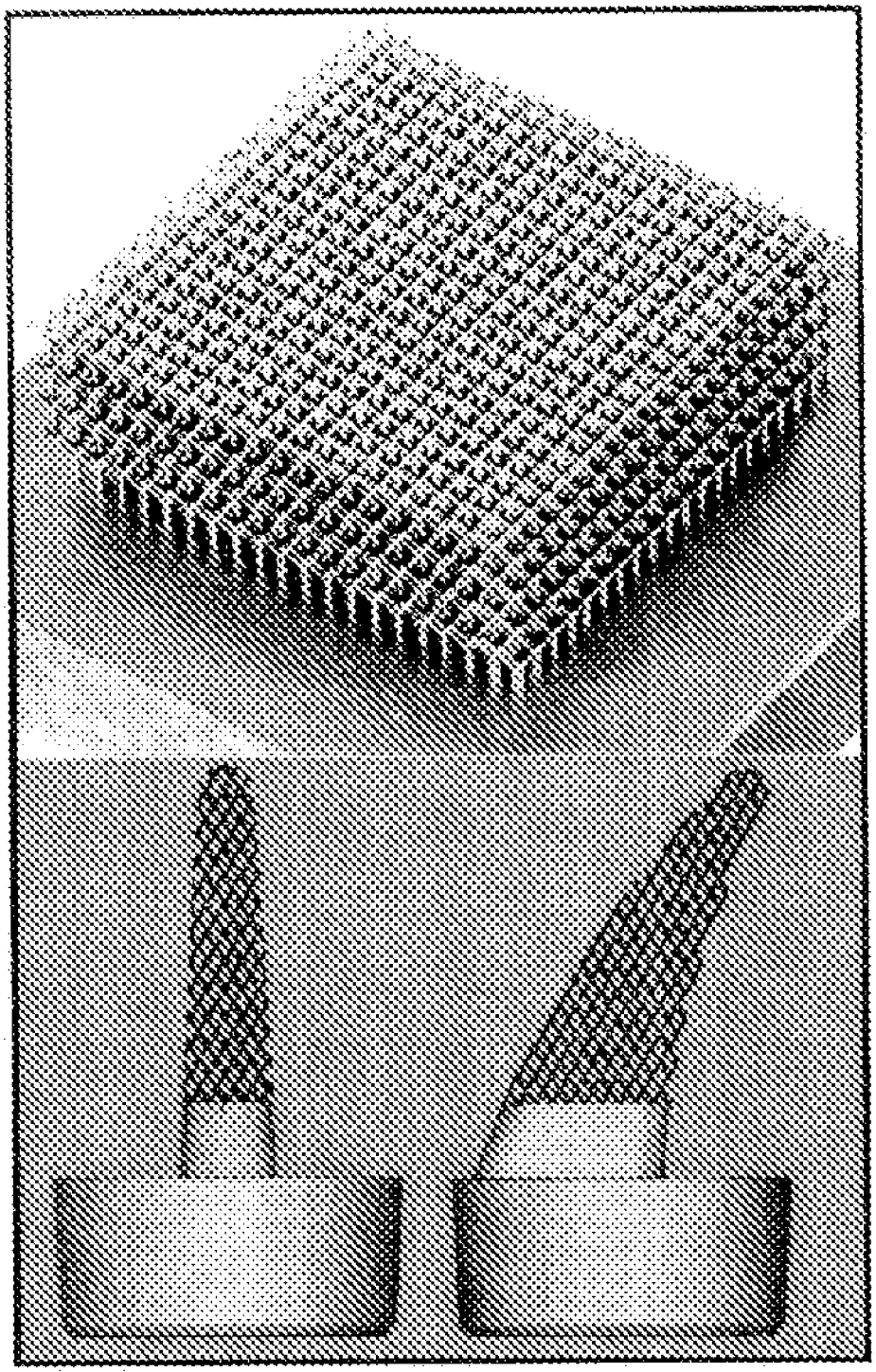
FIG. 30 shows typical freestanding structures.

A method for making lattice-type constructs was referred to in the relevant art. A typical example of this type of structure is shown in FIG. 30. The scanning strategy employed to form such a construct was mentioned and such a strategy could be produced within the range of Andrew numbers outlined. Table 4 shows an indication of scanning strategies and their relationships to the Andrew number.

TABLE 4

| LAYER | SCAN STRATEGY | PARAMETER SET | LAYER THICKNESS | RELATIVE BUILD PLATFORM POSITION | ADDITIONAL |
|---|---|---|---|---|---|
| Ti on Ta on CoCr Experimental Procedure. Initial Tantalum Coating | | | | | |
| Zero Distance Between Roller & Build Platform | | | | 0 | |
| 0 | 1$^{st}$ layer thickness set using feeler gauges but powder not laid in preparation for cleaning scan with no powder. | | 50 μm | −50 μm | |
| 1 | 50% Beam Overlap | P = 82 W<br>Qs = 30 kHz<br>v = 60 mm/s<br>A$_n$ = 27.333 J/mm² | | | Initial Cleaning Scan (no powder) |
| | Circular profile. 5 concentric circles, 0.1 mm offset to negate effects of 'First Pulse' | P = 82 W<br>Qs = 40 kHz<br>V = 160 mm/s<br>A$_n$ = 5.125 J/mm² | | | Powder laid as usual |
| | 50% Beam Overlap | P = 82 W<br>Qs = 30 kHz<br>v = 300 mm/s<br>A$_n$ = 5.467 J/mm² | | | Scanned on same powder layer as |

TABLE 4-continued

| LAYER | SCAN STRATEGY | PARAMETER SET | LAYER THICKNESS | RELATIVE BUILD PLATFORM POSITION | ADDITIONAL |
|---|---|---|---|---|---|
| | | | | | previous profile scan. |
| 2 | Circular profile. 5 concentric circles, 0.1 mm offset to negate effects of 'First Pulse' | P = 82 W<br>Qs = 40 kHz<br>V = 160 mm/s<br>$A_n$ = 5.125 J/mm$^2$ | 50 μm | −100 μm | Powder laid as usual |
| | 50% Beam Overlap | P = 82 W<br>Qs = 30 kHz<br>v = 300 mm/s<br>$A_n$ = 5.467 J/mm$^2$ | | | Scanned on same powder layer as previous profile scan. |
| 3 | Circular profile. 5 concentric circles, 0.1 mm offset to negate effects of 'First Pulse' | P = 82 W<br>Qs = 40 kHz<br>V = 160 mm/s<br>$A_n$ = 5.125 J/mm$^2$ | 50 μm | −150 μm | Powder laid as usual |
| | 50% Beam Overlap | P = 82 W<br>Qs = 30 kHz<br>v = 300 mm/s<br>$A_n$ = 5.467 J/mm$^2$ | | | Scanned on same powder layer as previous profile scan. |
| Final Titanium Coating ||||||
| 0 | 1$^{st}$ layer thickness set using feeler gauges but powder not laid in preparation for cleaning scan with no powder. | | | −150 μm | |
| 1 | 50% Beam Overlap | P = 82 W<br>Qs = 30 kHz<br>v = 60 mm/s<br>$A_n$ = 27.3 J/mm$^2$ | 50 μm | −200 μm | Cleaning Scan (No powder. |
| | Circular profile. 5 concentric circles, 0.1 mm offset to negate effects of 'First Pulse' | P = 82 W<br>Qs = 40 kHz<br>V = 160 mm/s<br>$A_n$ = 5.125 J/mm$^2$ | | | Powder spread but build platform not lowered. |
| | 50% Beam Overlap | P = 82 W<br>Qs = 30 kHz<br>v = 300 mm/s<br>$A_n$ = 5.467/mm$^2$ | | | Scanned on same powder layer as previous profile scan. |
| 2 | Circular profile. 5 concentric circles, | P = 82 W<br>Qs = 40 kHz<br>V = 160 mm/s<br>$A_n$ = 5.125 J/mm$^2$ | 100 μm | −300 μm | Powder laid as usual |

TABLE 4-continued

| LAYER | SCAN STRATEGY | PARAMETER SET | LAYER THICKNESS | RELATIVE BUILD PLATFORM POSITION | ADDITIONAL |
|---|---|---|---|---|---|
|  | 0.1 mm offset to negate effects of 'First Pulse' 25% Beam Overlap | $P = 82$ W $Qs = 30$ kHz $v = 300$ mm/s $A_n = 3.644$ J/mm$^2$ |  |  | Scanned on same powder layer as previous profile scan. |
| 3 | Circular profile. 5 concentric circles, 0.1 mm offset to negate effects of 'First Pulse' | $P = 82$ W $Qs = 40$ kHz $V = 160$ mm/s $A_n = 5.125$ J/mm$^2$ | 100 μm | −400 μm | Powder laid as usual |
|  | 0% Beam Overlap | $P = 82$ W $Qs = 30$ kHz $v = 300$ mm/s $A_n = 2.733$ J/mm$^2$ |  |  | Scanned on same powder layer as previous profile scan. |
| 4 | Waffle 0 and 90° 700 μm linespacing (−600% Beam overlap) | $P = 82$ W $Qs = 0$ Hz (cw) $v = 240$ mm/s $A_n = 0.488$ J/mm$^2$ | 75 μm | −475 μm | Powder laid as usual |
| 5 | Waffle 0 and 90° 700 μm linespacing (−600% Beam overlap) | $P = 82$ W $Qs = 0$ Hz (cw) $v = 240$ mm/s $A_n = 0.488$ J/mm$^2$ | 75 μm | −550 μm | Powder laid as usual |
| 6 | Waffle 0 and 90° 700 μm linespacing (−600% Beam overlap) | $P = 82$ W $Qs = 0$ Hz (cw) $v = 240$ mm/s $A_n = 0.488$ J/mm$^2$ | 75 μm | −625 μm | Powder laid as usual |
| 7 | Waffle 45 and 135° 700 μm linespacing (−600% Beam overlap) | $P = 82$ W $Qs = 0$ Hz (cw) $v = 240$ mm/s $A_n = 0.488$ J/mm$^2$ | 75 μm | −700 μm | Powder laid as usual |
| 8 | Waffle 45 and 135° 700 μm linespacing (−600% Beam overlap) | $P = 82$ W $Qs = 0$ Hz (cw) $v = 240$ mm/s $A_n = 0.488$ J/mm$^2$ | 75 μm | −775 μm | Powder laid as usual |
| 9 | Waffle 45 and 135° 700 μm linespacing (−600% Beam overlap) | $P = 82$ W $Qs = 0$ Hz (cw) $v = 240$ mm/s $A_n = 0.488$ J/mm$^2$ | 75 μm | −850 μm | Powder laid as usual |

TABLE 4-continued

| LAYER | SCAN STRATEGY | PARAMETER SET | LAYER THICKNESS | RELATIVE BUILD PLATFORM POSITION | ADDITIONAL |
|---|---|---|---|---|---|
| Ti on Ti Experimental Procedure. Initial Titanium Coating ||||||
| Zero Distance Between Roller & Build Platform | | | | 0 | |
| 0 | $1^{st}$ layer thickness set using feeler gauges but powder not laid in preparation for cleaning scan with no powder. | | 50 μm | −50 μm | |
| 1 | 50% Beam Overlap | P = 82 W<br>Qs = 30 kHz<br>v = 60 mm/s<br>$A_n$ = 27.333 J/mm$^2$ | | | Initial Cleaning Scan (no powder) |
| | Circular profile. 5 concentric circles, 0.1 mm offset to negate effects of 'First Pulse' | P = 82 W<br>Qs = 40 kHz<br>V = 160 mm/s<br>$A_n$ = 5.125 J/mm$^2$ | | | Powder laid as usual |
| | 50% Beam Overlap | P = 82 W<br>Qs = 30 kHz<br>v = 300 mm/s<br>$A_n$ = 5.467 J/mm$^2$ | | | Scanned on same powder layer as previous profile scan. |
| 2 | Circular profile. 5 concentric circles, 0.1 mm offset to negate effects of 'First Pulse' | P = 82 W<br>Qs = 40 kHz<br>V = 160 mm/s<br>$A_n$ = 5.125 J/mm$^2$ | 50 μm | −100 μm | Powder laid as usual |
| | 50% Beam Overlap | P = 82 W<br>Qs = 30 kHz<br>v = 300 mm/s<br>$A_n$ = 5.467 J/mm$^2$ | | | Scanned on same powder layer as previous profile scan. |
| 3 | Circular profile. 5 concentric circles, 0.1 mm offset to negate effects of 'First Pulse' | P = 82 W<br>Qs = 40 kHz<br>V = 160 mm/s<br>$A_n$ = 5.125 J/mm$^2$ | 50 μm | −150 μm | Powder laid as usual |
| | 50% Beam Overlap | P = 82 W<br>Qs = 30 kHz<br>v = 300 mm/s<br>$A_n$ = 5.467 J/mm$^2$ | | | Scanned on same powder layer as previous profile scan. |

TABLE 4-continued

| LAYER | SCAN STRATEGY | PARAMETER SET | LAYER THICKNESS | RELATIVE BUILD PLATFORM POSITION | ADDITIONAL |
|---|---|---|---|---|---|
| | | Final Titanium Coating | | | |
| 1 | Circular profile. 5 concentric circles, 0.1 mm offset to negate effects of 'First Pulse' | P = 82 W<br>Qs = 40 kHz<br>V = 160 mm/s<br>$A_n$ = 5.125 J/mm² | 100 μm | −250 μm | Powder laid as usual |
| | 50% Beam Overlap | P = 82 W<br>Qs = 30 kHz<br>v = 300 mm/s<br>$A_n$ = 5.467 J/mm² | | | Scanned on same powder layer as previous profile scan |
| 2 | Circular profile. 5 concentric circles, 0.1 mm offset to negate effects of 'First Pulse' | P = 82 W<br>Qs = 40 kHz<br>V = 160 mm/s<br>$A_n$ = 5.125 J/mm² | 100 μm | −350 μm | Powder laid as usual |
| | 25% Beam Overlap | P = 82 W<br>Qs = 30 kHz<br>v = 300 mm/s<br>$A_n$ = 3.644 J/mm² | | | Scanned on same powder layer as previous profile scan. |
| 3 | Circular profile. 5 concentric circles, 0.1 mm offset to negate effects of 'First Pulse' | P = 82 W<br>Qs = 40 kHz<br>V = 160 mm/s<br>$A_n$ = 5.125 J/mm² | 100 μm | −450 μm | Powder laid as usual |
| | 0% Beam Overlap | P = 82 W<br>Qs = 30 kHz<br>v = 300 mm/s<br>$A_n$ = 2.733 J/mm² | | | Scanned on same powder layer as previous profile scan. |
| 4 | Waffle 0 and 90° 700 μm linespacing (−600% Beam overlap) | P = 82 W<br>Qs = 0 Hz (cw)<br>v = 240 mm/s<br>$A_n$ = 0.488 J/mm² | 75 μm | −525 μm | Powder laid as usual |
| 5 | Waffle 0 and 90° 700 μm linespacing (−600% Beam overlap) | P = 82 W<br>Qs = 0 Hz (cw)<br>v = 240 mm/s<br>$A_n$ = 0.488 J/mm² | 75 μm | −600 μm | Powder laid as usual |
| 6 | Waffle 0 and 90° 700 μm linespacing (600% Beam overlap) | P = 82 W<br>Qs = 0 Hz (cw)<br>v = 240 mm/s<br>$A_n$ = 0.488 J/mm² | 75 μm | −675 μm | Powder laid as usual |
| 7 | Waffle 45 and 135° 700 μm linespacing (−600% Beam overlap) | P = 82 W<br>Qs = 0 Hz (cw)<br>v = 240 mm/s<br>$A_n$ = 0.488 J/mm² | 75 μm | −750 μm | Powder laid as usual |

TABLE 4-continued

| LAYER | SCAN STRATEGY | PARAMETER SET | LAYER THICKNESS | RELATIVE BUILD PLATFORM POSITION | ADDITIONAL |
|---|---|---|---|---|---|
| 8 | Waffle 45 and 135° 700 µm linespacing (−600% Beam overlap) | P = 82 W Qs = 0 Hz (cw) v = 240 mm/s $A_n$ = 0.488 J/mm$^2$ | 75 µm | −825 µm | Powder laid as usual |
| 9 | Waffle 45 and 135° 700 µm linespacing (−600% Beam overlap) | P = 82 W Qs = 0 Hz (cw) v = 240 mm/s $A_n$ = 0.488 J/mm$^2$ | 75 µm | −900 µm | Powder laid as usual |

Figure 31:
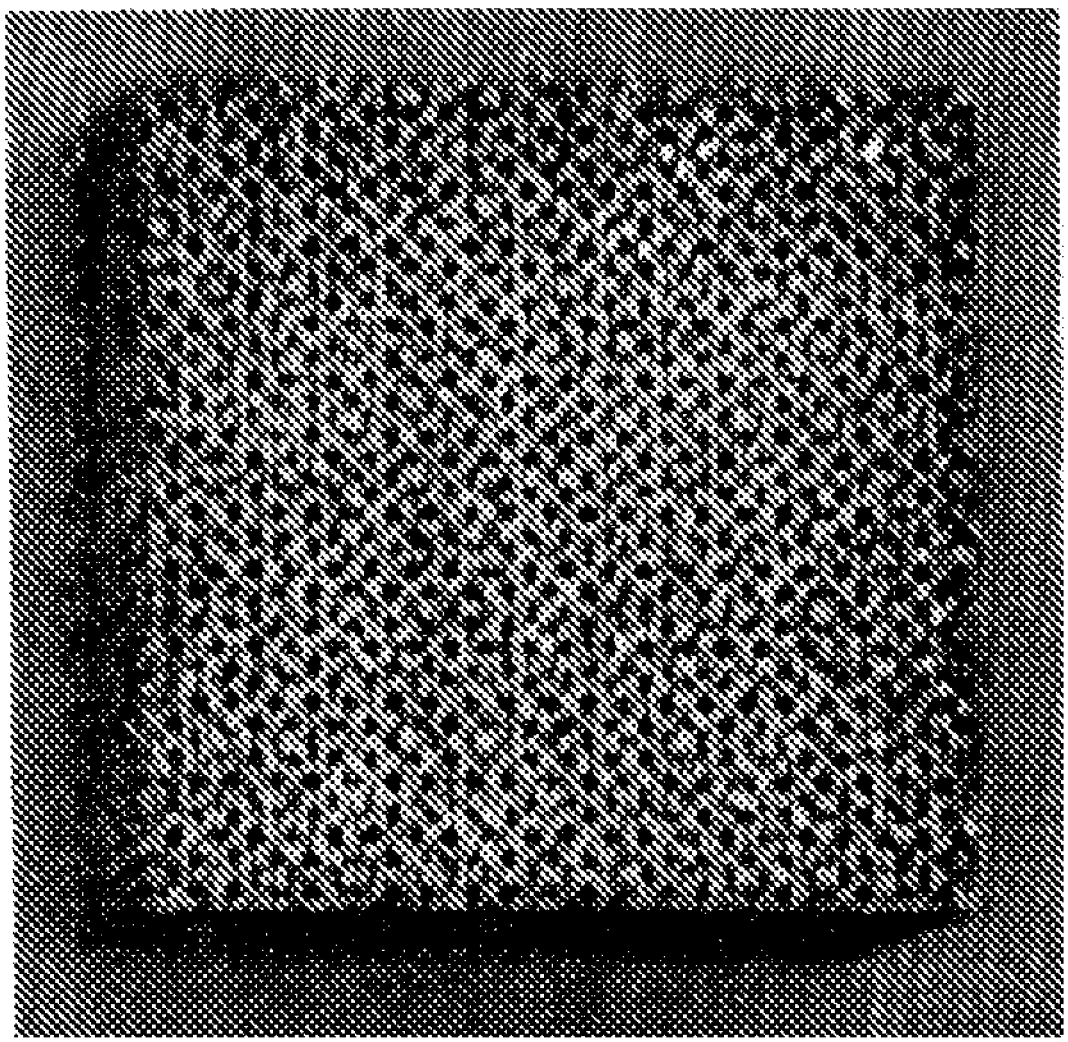
FIG. 31 shows a freestanding structure built using the preferred scanning strategy.

The second and preferred approach uses a continuous scanning strategy whereby the pores are developed by the planar deposition of laser melted powder tracks superimposed over each other. This superimposition combined with the melt flow produces random and pseudorandom porous structures. The properties of the final structure, randomness, interconnectivity, mechanical strength and thermal response are controlled by the process parameters employed. One set of scanning parameters used was: Scanning sequences of 0° 0° 0°, 90° 90° 90°, 45° 45° 45°, 135°, 135°, 135°, of layer thickness 0.1 mm were developed to form a waffle. Three layers of each were necessary to obtain sufficient web thickness in the "z" direction. The array of sequences was repeated many times to give a construct of the desired height. Laser power was 82 watts, operating frequency between 0 (cw) and 40 KHz, scan speed of between 160 and 240 mm/sec with a beam overlap of −700%. FIG. 31 shows such a construct.

The use of an optical inspection method to determine this approximate porosity is appropriate given the sample size. This method, although not accurate due to the filter selection process, can, if used carefully, provide an indication of porosity. An average porosity level of around 25% was predicted. This porosity level falls within the range of the desired porosity for bone in-growth structures.

In consideration of the potential application, it is important to minimize loose surface contamination and demonstrate the ability to fully clean the surface. Laser cleaning or acid etching technique may be effective. Additionally, a rigorous cleaning protocol to remove all loose powder may entail blowing the porous structure with clean dry compressed gas, followed by a period of ultrasonic agitation in a treatment fluid. Once dried, a laser scan may be used to seal any remaining loose particles.

On examination, all candidate materials and substrates were selectively fused to produce a complex interconnected pore structure. There were small differences in certain process parameters such as speed and beam overlap percentage. From FIG. 12 it can also be seen how the Ti build has successfully fused with the Ti alloy substrate using a laser power of 82 W cw, beam overlap of −40% and a laser scanning speed of 180 mms$^{-1}$. With the ability to produce structures with a controlled porosity, this demonstrates how the Direct Laser Remelting process can be used as a surface modification technology. Certain metal combinations interacted unfavourably and resulted in formation of intermetallics, which are inherently brittle structures. To overcome this problem it may be necessary to use a bond coat with the substrate. It is then possible to build directly on to the substrate with a porous build. A typical example of the use of a bond coat is provided by the combination of titanium on to a cobalt chromium substrate. Tantalum also was an effective bond coat in this example. Note that the bond coat may be applied by laser technology, but other methods are also possible such as gas plasma deposition.

Figure 14A:
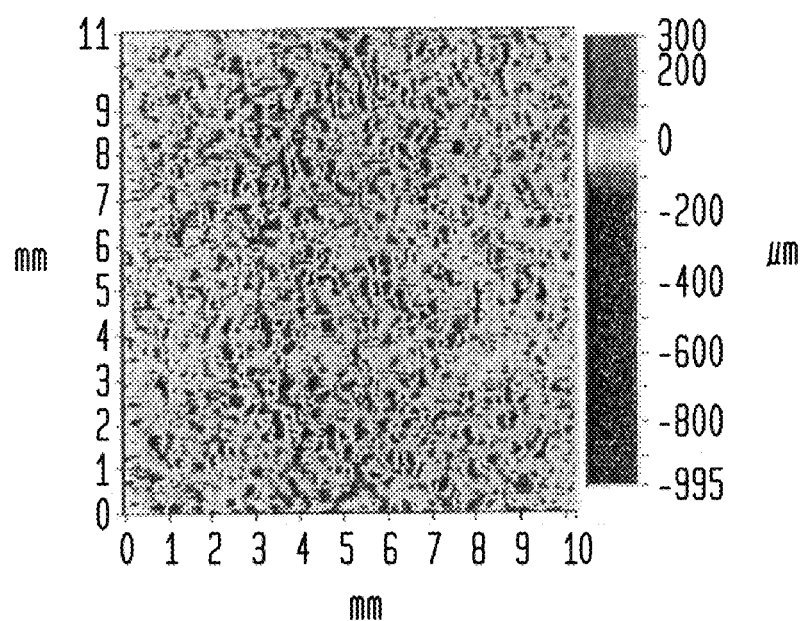
FIGS. 14 and 15 are non-contact surface profilimetry images detailing plan views of the samples.
Figure 14B:
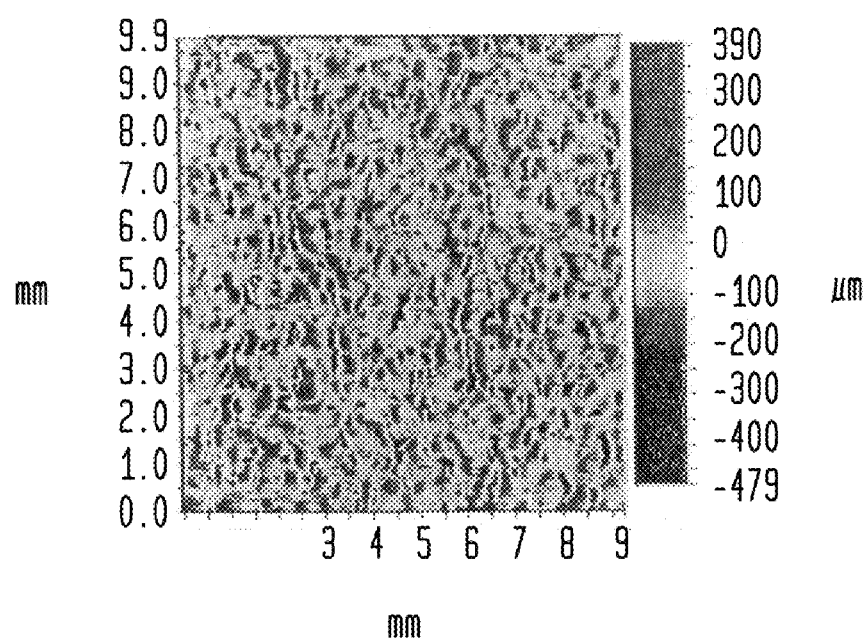
Figure 15A:
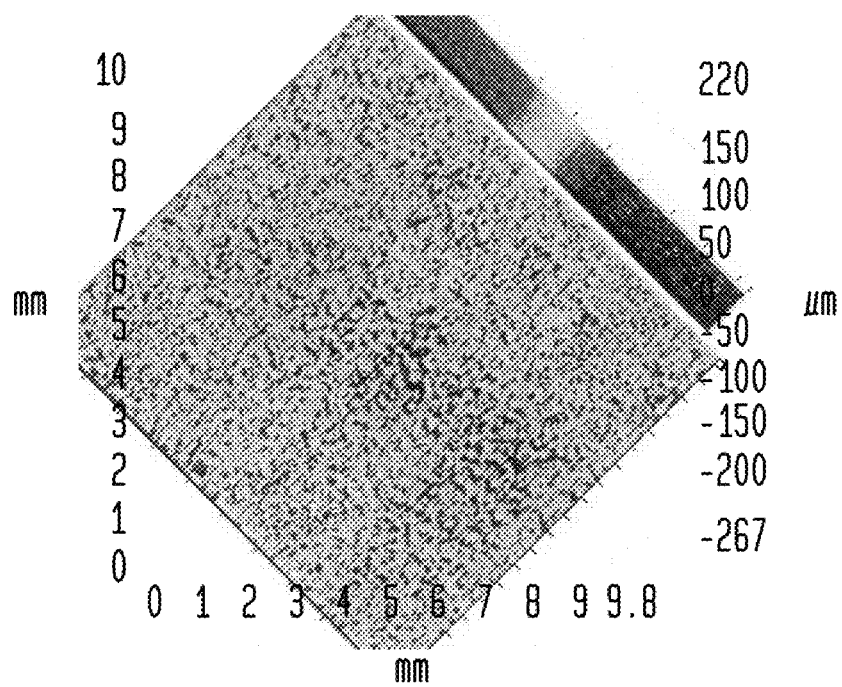
Figure 15B:
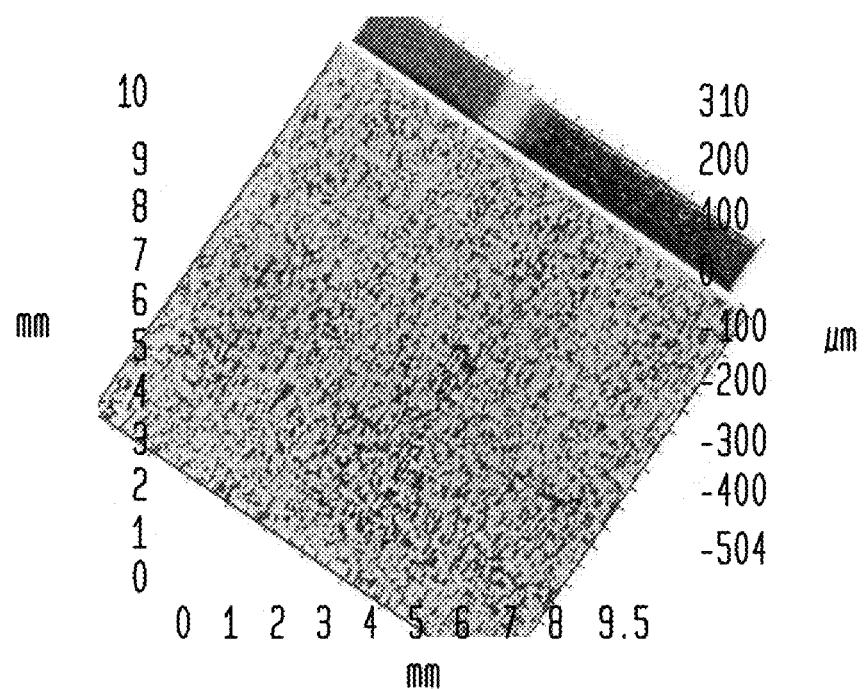

The non-contact surface profilimeotry (OSP) images shown in FIGS. 13(a) to 13(d) show the surface profile. In addition, the Surface Data shown in FIGS. 14(a) and 14(b) and 15(a) and 15(b) show a coded profile of the plan views of the samples. FIG. 14(a) shows Ti on Ti (OSP Surface Data) where v=200 mms$^{-1}$, FIG. 14(b) shows CoCr on Ti (OSP Surface Data) where v=200 mms$^{-1}$, and FIG. 15(a) shows Nb on Ti (OSP Surface Data) where v=200 mms$^{-1}$ and FIG. 15(b) shows Ta on Ti (OSP Surface Data) where v=200 mms$^{-1}$.

FIGS. 16 to 25 are scanning electron microscope (SEM) micrographs of a series of single layer Ti on CoCr and Ti on Ti images that were produced prior to the multi-layer builds shown in FIGS. 8 and 9 respectively and as follows.

Figure 16A:
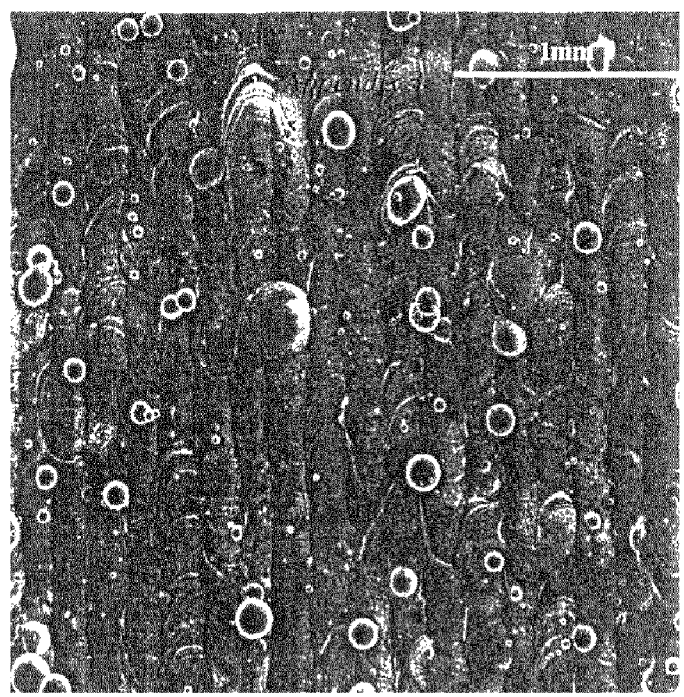
FIGS. 16 to 25 are scanning electron microscope micrographs produced prior to multi-layer builds shown in FIGS. 7 and 8.
Figure 16B:
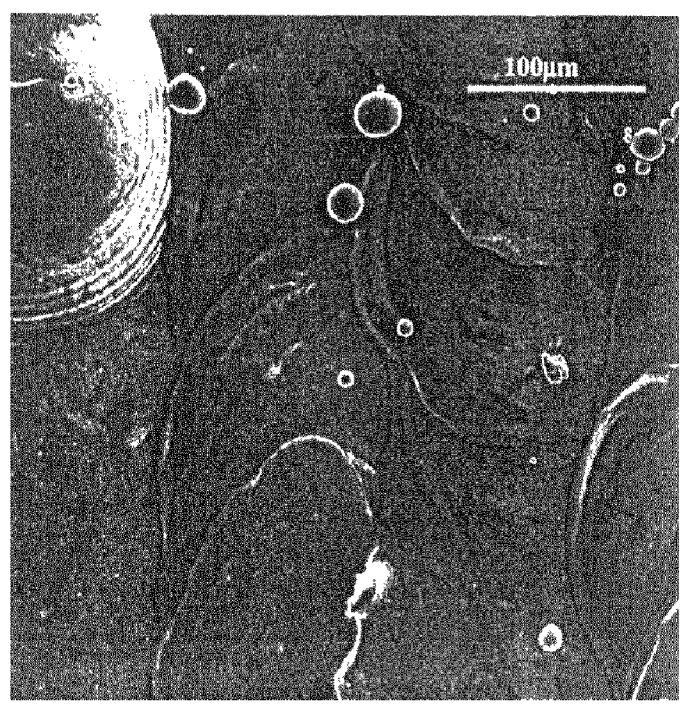
Figure 17A:
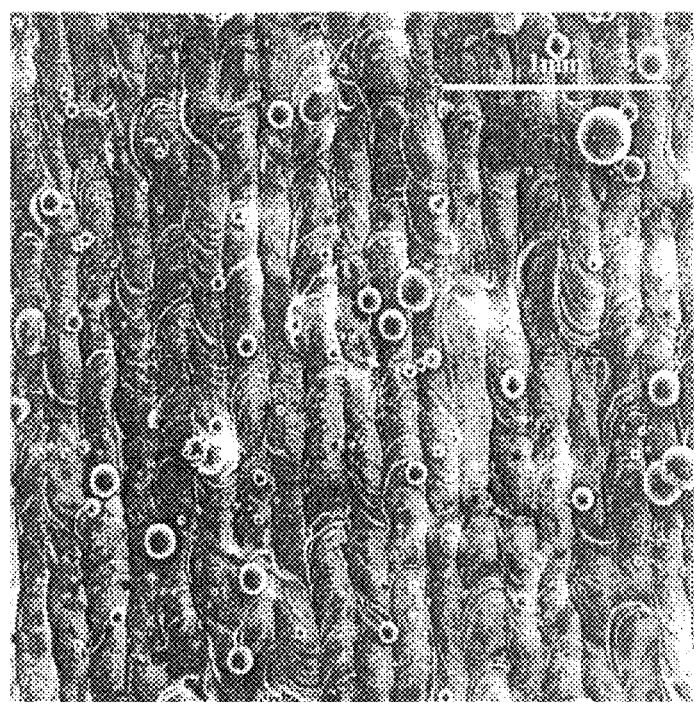
Figure 17B:
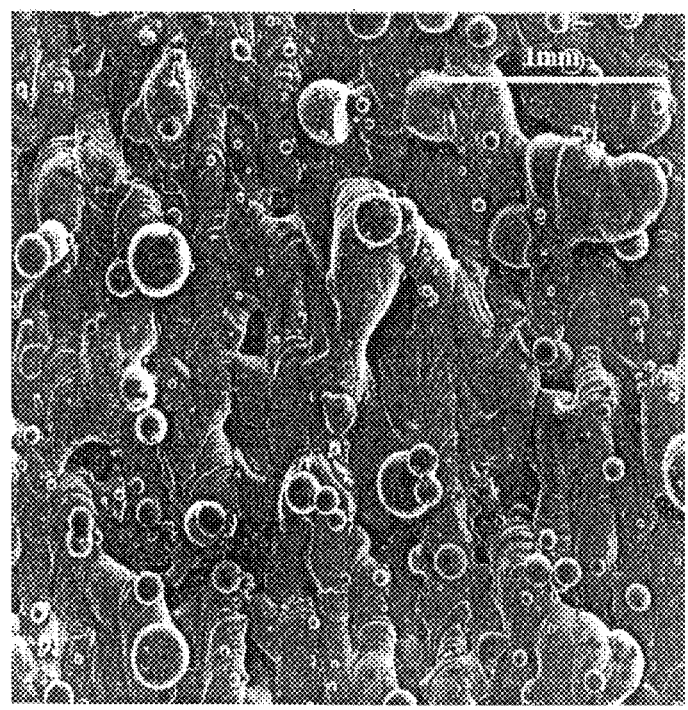
Figure 18A:
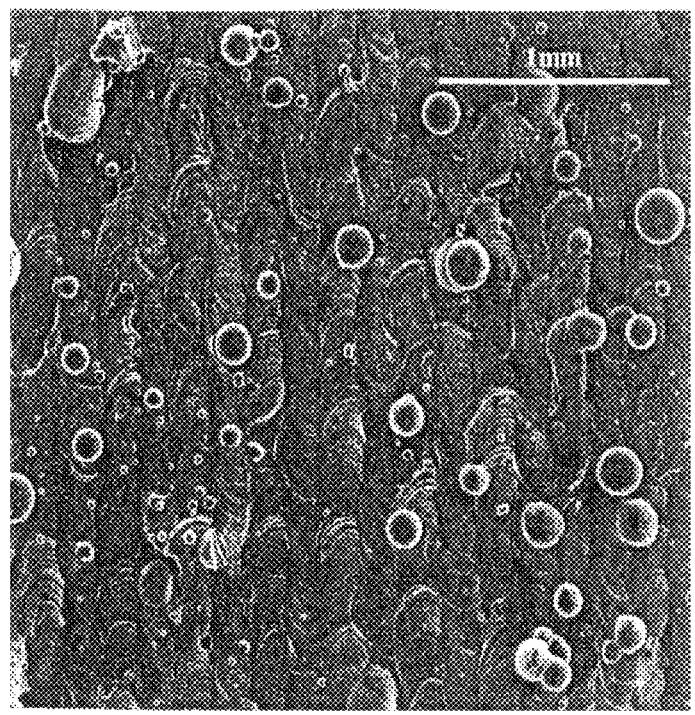
Figure 18B:
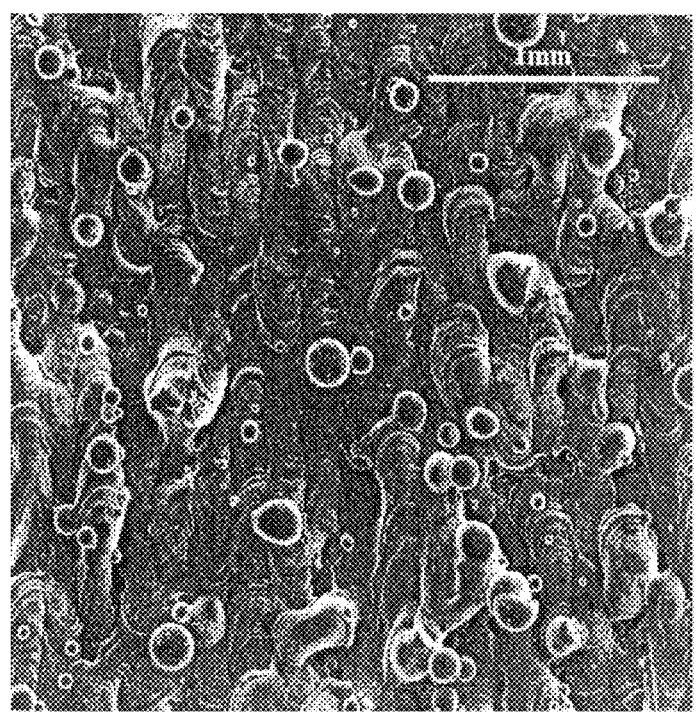
Figure 19A:
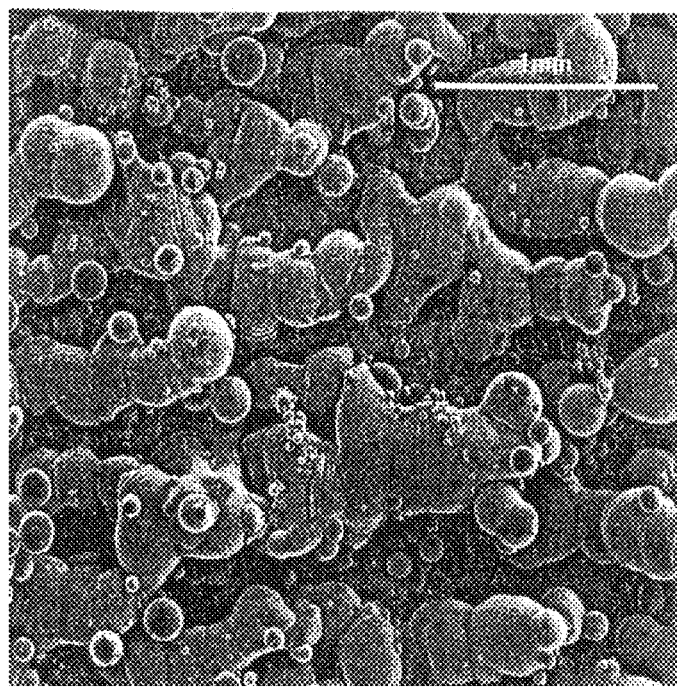
Figure 19B:
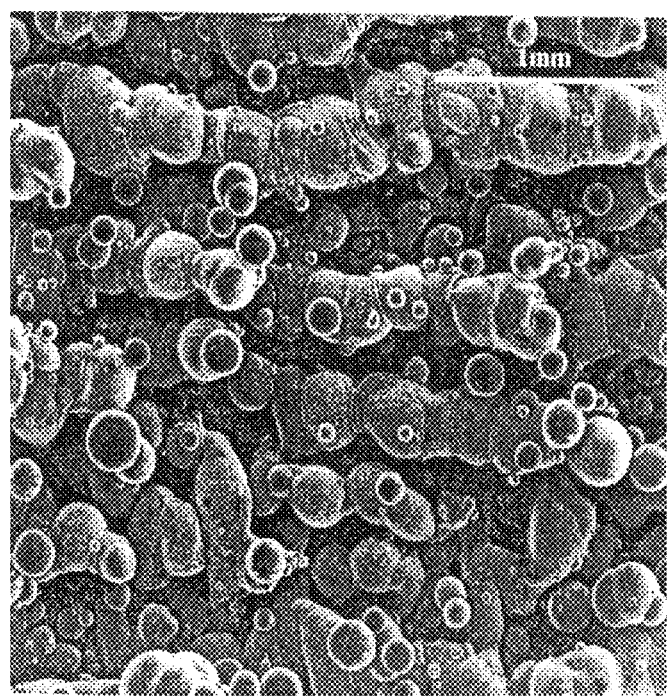
Figure 20A:
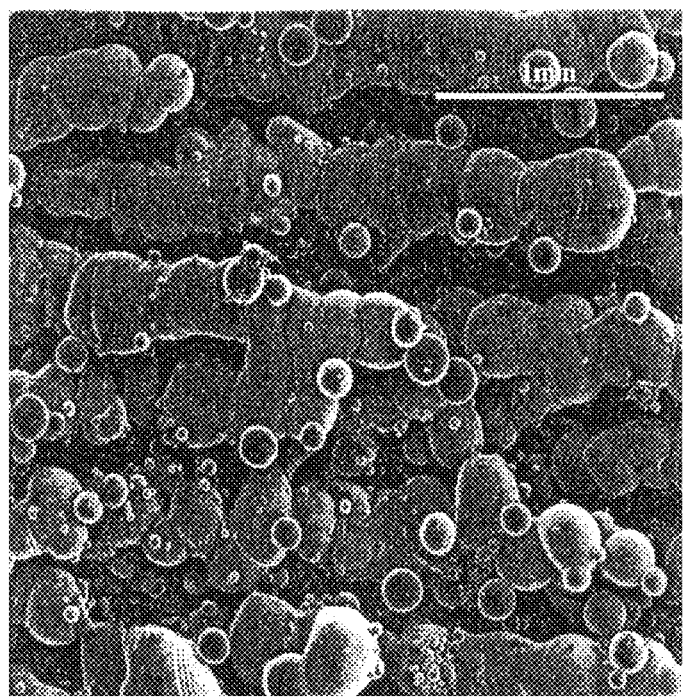
Figure 20B:
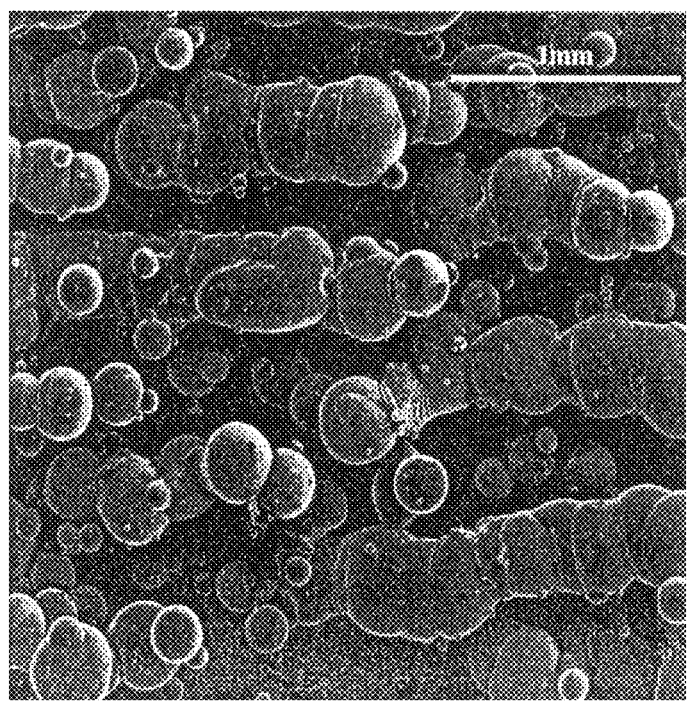
Figure 21A:
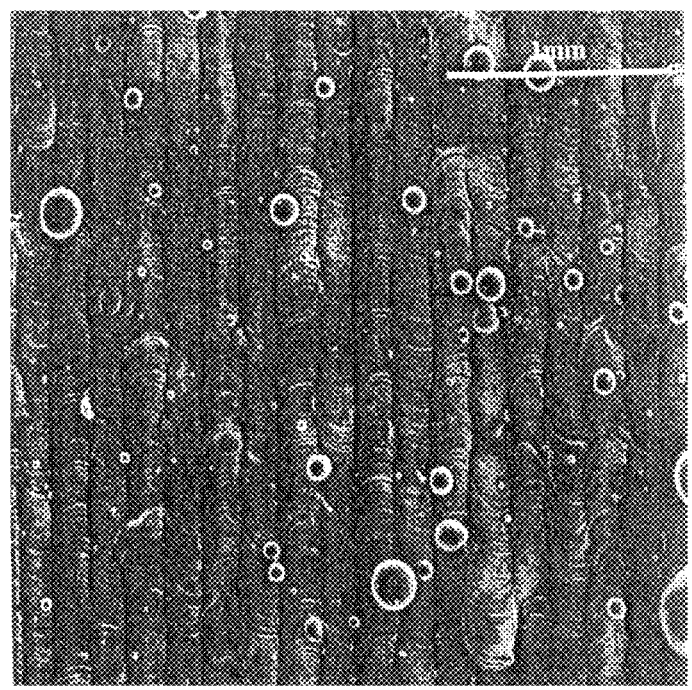
Figure 21B:
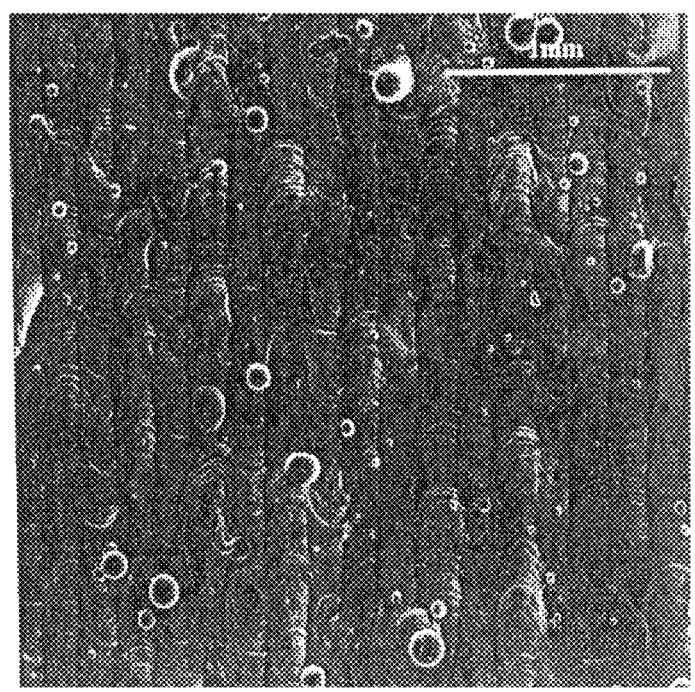
Figure 22A:
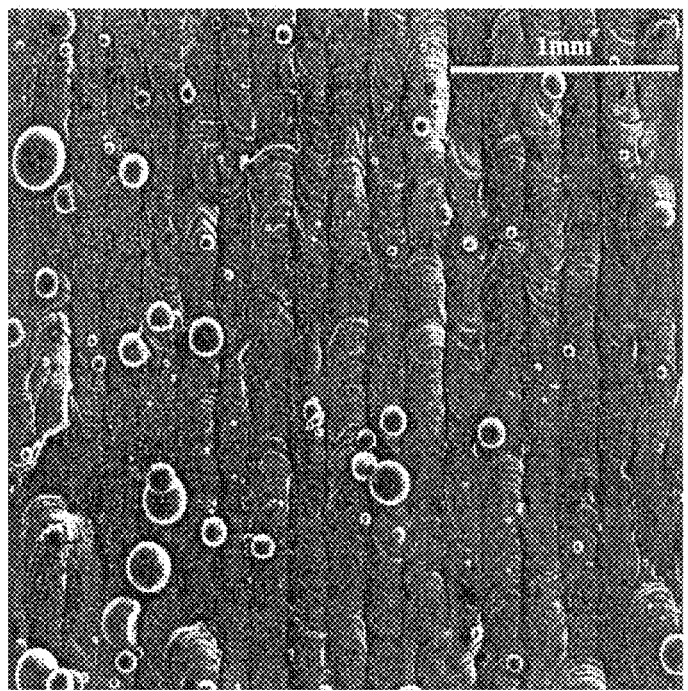
Figure 22B:
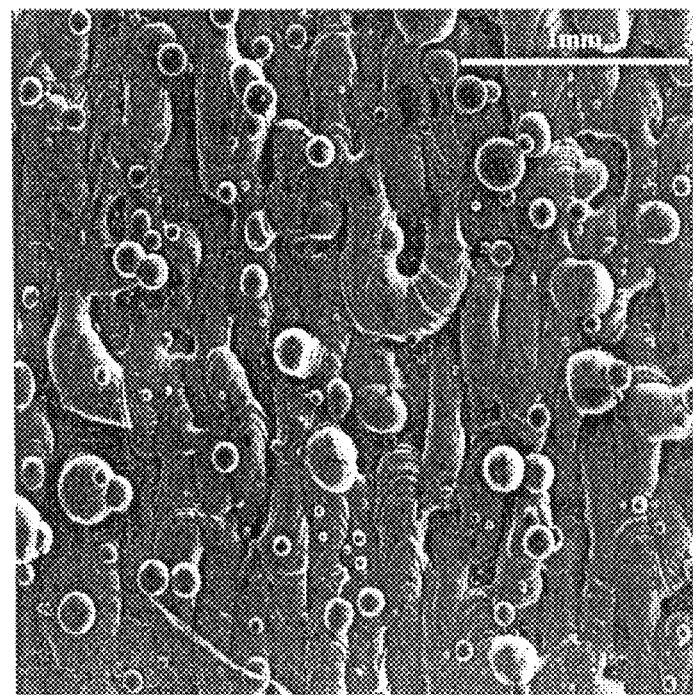
Figure 23A:
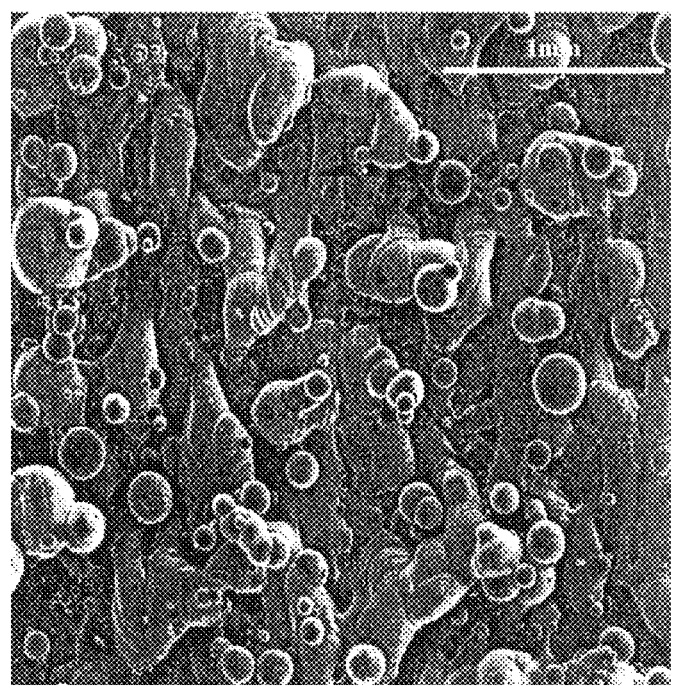
Figure 23B:
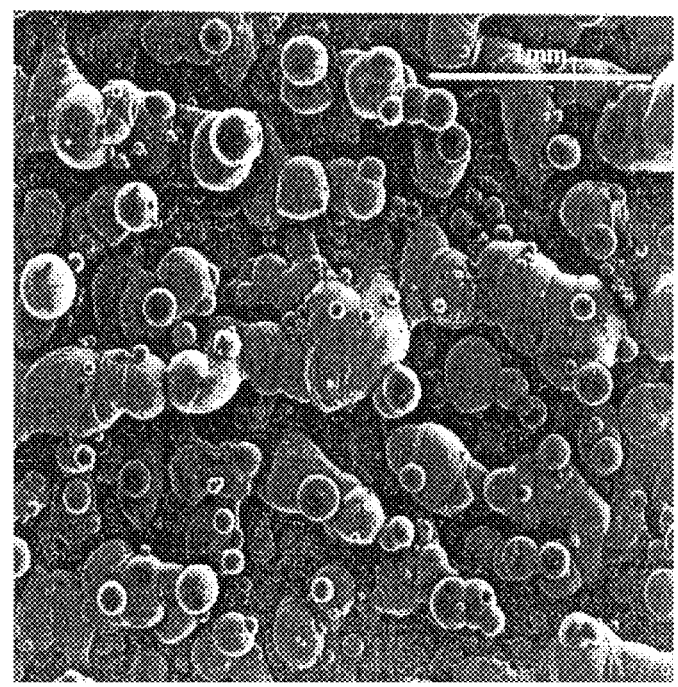
Figure 24A:
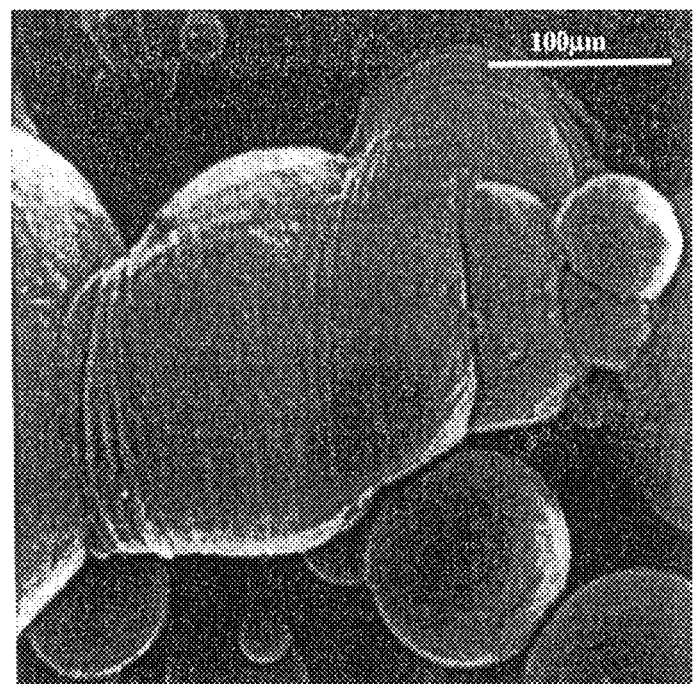
Figure 24B:
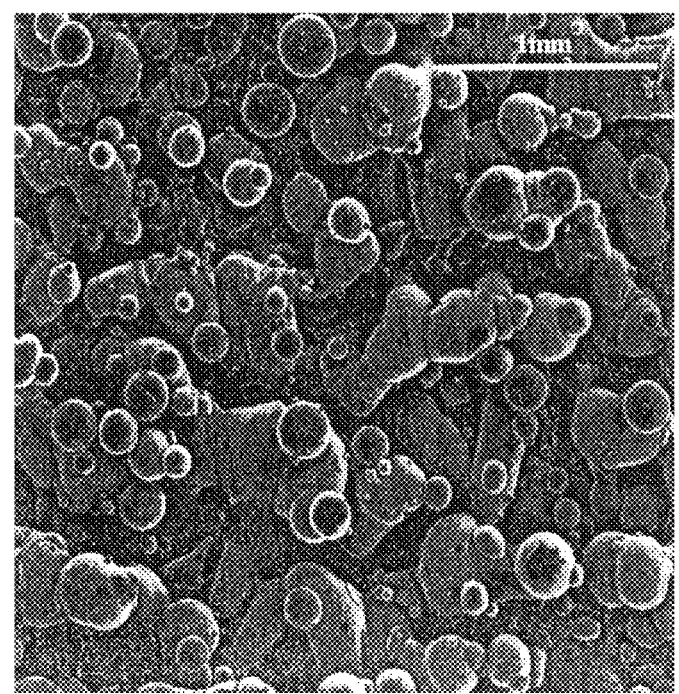
Figure 25:
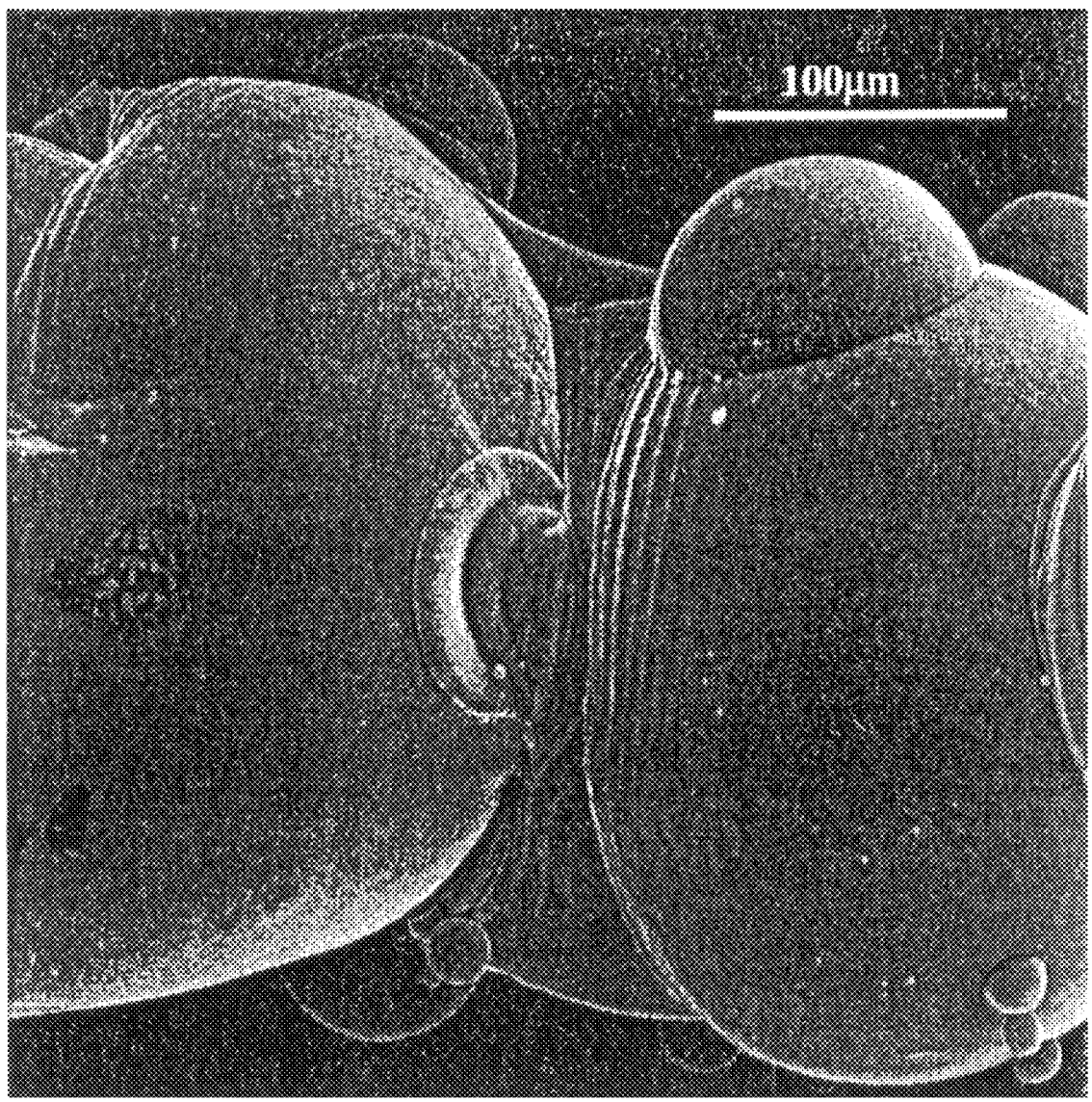

FIG. 16(a) shows Ti on CoCr (Single Layer; SEM Micrograph) v=160 mms$^{-1}$;
FIG. 16(b) shows Ti on CoCr (Single Layer; SEM Micrograph) v=160 mms$^{-1}$;
FIG. 17(a) shows Ti on CoCr (Single Layer; SEM Micrograph) v=170 mms$^{-1}$;
FIG. 17(b) shows Ti on CoCr (Single Layer; SEM Micrograph) v=180 mms$^{-1}$;
FIG. 18(a) shows Ti on CoCr (Single Layer; SEM Micrograph) v=190 mms$^{-1}$;
FIG. 18(b) shows Ti on CoCr (Single Layer; SEM Micrograph) v=200 mms$^{-1}$;
FIG. 19(a) shows Ti on CoCr (Single Layer; SEM Micrograph) v=210 mms$^{-1}$;
FIG. 19(b) shows Ti on CoCr (Single Layer; SEM Micrograph) v=220 mms$^{-1}$;
FIG. 20(a) shows Ti on CoCr (Single Layer; SEM Micrograph) v=230 mms$^{-1}$;
FIG. 20(b) shows Ti on CoCr (Single Layer; SEM Micrograph) v=240 mms$^{-1}$;
FIG. 21(a) shows Ti on Ti (Single Layer; SEM Micrograph) v=160 mms$^{-1}$;
FIG. 21(b) shows Ti on Ti (Single Layer; SEM Micrograph) v=170 mms$^{-1}$;
FIG. 22(a) shows Ti on Ti (Single Layer; SEM Micrograph) v=190 mms$^{-1}$;
FIG. 22(b) shows Ti on Ti (Single Layer; SEM Micrograph) v=200 mms$^{-1}$;
FIG. 23(a) shows Ti on Ti (Single Layer; SEM Micrograph) v=220 mms$^{-1}$;

FIG. 23(b) shows Ti on Ti (Single Layer; SEM Micrograph) v=230 mms$^{-1}$;

FIG. 24(a) shows Ti on Ti (Single Layer; SEM Micrograph) v=240 mms$^{-1}$;

FIG. 24(b) shows Ti on Ti (Single Layer; SEM Micrograph) v=240 mms$^{-1}$;

The method according to the present invention can produce surface structures on all powder/baseplate combinations with careful selection of process parameters.

As described above, the process is carried out on flat baseplates that provide for easy powder delivery in successive layers of around 100 μm thickness. Control of powder layer thickness is very important if consistent surface properties are required. The application of this technology can also be applied to curved surfaces such as those found in modern prosthetic devices; with refinements being made to the powder layer technique.

The structures have all received ultrasonic and aqueous cleaning. On close examination, the resultant porous surfaces produced by the Direct Laser Remelting process exhibit small particulates that are scattered throughout the structure. It is unclear at this stage whether these particulates are bonded to the surface or loosely attached but there are means to remove the particulates if required.

The Direct Laser Remelting process has the ability to produce porous structures that are suitable for bone in-growth applications. The powdered surfaces have undergone considerable thermal cycling culminating in rapid cooling rates that have produced very fine dendritic structures (e.g. FIGS. 13(a) to 13(d)).

The Direct Laser Remelting process can produce effective bone in-growth surfaces and the manufacturing costs are reasonable.

In the preceding examples, the object has been to provide a porous structure on a base but the present invention can also be used to provide a non-porous structure on such a base to form a three-dimensional structure. The same techniques can be utilized for the materials concerned but the laser processing parameters can be appropriately selected so that a substantially solid non-porous structure is achieved.

Again, a technique can be used to deposit the powder onto a suitable carrier, for example a mold, and to carry out the process without the use of a base so that a three-dimensional structure is achieved which can be either porous, as described above, or non-porous if required.

It will be appreciated that this method can, therefore, be used to produce article from the metals referred to which can be created to a desired shape and which may or may not require subsequent machining. Yet again, such an article can be produced so that it has a graded porosity of, e.g., non-porous through various degrees of porosity to the outer surface layer. Such articles could be surgical prostheses, parts or any other article to which this method of production would be advantageous.

The invention claimed is:

1. A method of producing a three-dimensional porous tissue ingrowth structure comprising:
    depositing a first layer of a metal powder onto a substrate;
    scanning a beam having a negative beam overlap at least once over at least a portion of the first layer of metal powder to remelt at least a portion of the metal powder in order to create at least two solid portions separated from one another so as to control porosity;
    depositing a second layer of the metal powder onto the first layer; and
    repeating the scanning steps for each successive layer until a desired height is reached.

2. The method according to claim 1, wherein the metal powder is selected from the group consisting of titanium, titanium alloys, stainless steel, cobalt chrome alloys, tantalum and niobium.

3. The method according to claim 1, wherein during the step of repeating the scanning steps, at least one scan is carried out angled relative to another scan in order to develop an interconnecting or non-interconnecting porosity.

4. The method according to claim 1, wherein the thickness of each of the first layer and the successive layers of powder is between 5 μm-2000 μm.

5. The method according to claim 1, wherein the substrate is a base or core made of a metal selected from the group consisting of titanium, titanium alloys, stainless steel, cobalt chrome alloys, tantalum and niobium, wherein the first layer is fused to the base or core.

6. The method according to claim 1, wherein the method is carried out under an inert atmosphere.

7. A method of producing a three-dimensional porous tissue ingrowth structure comprising:
    depositing a first layer of metal powder onto a substrate;
    scanning a beam having a power and a diameter and a negative beam overlap over the metal powder to remelt the metal powder in order to create at least two solid lines so as to control porosity, the negative beam overlap allowing for a non-solid space between the two solid lines; and
    depositing at least one additional layer of the metal powder onto the first layer and repeating the scanning steps for each successive layer.

8. The method according to claim 7, wherein the beam is a laser beam.

9. The method according to claim 7, wherein the metal powder is selected from the group consisting of titanium, titanium alloys, stainless steel, cobalt chrome alloys, tantalum and niobium.

10. The method according to claim 7, wherein the thickness of each of the layers is between 50 μm-2000 μm.

11. The method according to claim 7, wherein the substrate is a base or core made of a metal selected from the group consisting of titanium, titanium alloys, stainless steel, cobalt chrome alloys, tantalum and niobium, wherein the first layer is fused to the base or core.

12. The method according to claim 11, wherein the thickness of the powder is approximately 100 μm.

13. The method according to claim 7, wherein the method is carried out under an inert atmosphere.

14. The method according to claim 7, comprising the additional step of subjecting a powder layer to a second beam scan with a scanning speed and beam overlap in an orthogonal direction to a first scan.

15. A method of producing a three-dimensional porous tissue ingrowth structure comprising:
    providing a substrate made of a metal selected from selected from the group consisting of titanium, titanium alloys, stainless steel, cobalt chrome alloys, tantalum and niobium;
    depositing a first layer of a metal powder onto the substrate, the metal powder selected from the group consisting of titanium, titanium alloys, stainless steel, cobalt chrome alloys, tantalum and niobium;
    scanning a beam having a negative beam overlap at least once over at least a portion of the first layer of metal powder to remelt at least a portion of the metal powder in order to create at least two solid portions separated from one another so as to control porosity;

depositing a second layer of metal powder onto the first layer; and repeating the scanning steps for each successive layer until a desired height is reached, wherein during the step of repeating the scanning steps, at least one scan is carried out angled relative to another scan in order to develop an interconnecting or non-interconnecting porosity.

* * * * *